(12) United States Patent
Hjelmgaard

(10) Patent No.: US 11,820,116 B2
(45) Date of Patent: Nov. 21, 2023

(54) BINDER COMPOSITION

(71) Applicant: ROCKWOOL INTERNATIONAL A/S, Hedehusene (DK)

(72) Inventor: Thomas Hjelmgaard, Fredensborg (DK)

(73) Assignee: ROCKWOOL A/S, Hedehusene (DK)

( * ) Notice: Subject to any disclaimer, the term of this patent is extended or adjusted under 35 U.S.C. 154(b) by 1253 days.

(21) Appl. No.: 16/099,321

(22) PCT Filed: May 11, 2017

(86) PCT No.: PCT/EP2017/061418
§ 371 (c)(1),
(2) Date: Nov. 6, 2018

(87) PCT Pub. No.: WO2017/194724
PCT Pub. Date: Nov. 16, 2017

(65) Prior Publication Data
US 2020/0317921 A1    Oct. 8, 2020

(30) Foreign Application Priority Data

May 13, 2016  (EP) ..................................... 16169635
May 13, 2016  (EP) ..................................... 16169638
May 13, 2016  (EP) ..................................... 16169641

(51) Int. Cl.
*B32B 37/12*    (2006.01)
*C09J 101/28*   (2006.01)
(Continued)

(52) U.S. Cl.
CPC ............... *B32B 37/12* (2013.01); *B32B 5/12* (2013.01); *B32B 5/26* (2013.01); *B32B 7/12* (2013.01); *B32B 15/14* (2013.01); *B32B 19/04* (2013.01); *B32B 19/041* (2013.01); *B32B 37/1207* (2013.01); *B32B 37/146* (2013.01); *B32B 37/18* (2013.01); *B32B 38/0004* (2013.01); *C03C 13/06* (2013.01); *C03C 25/26* (2013.01); *C03C 25/32* (2013.01); *C03C 25/321* (2013.01); *C03C 25/328* (2013.01); *C08J 5/043* (2013.01); *C08L 1/286* (2013.01); *C08L 3/02* (2013.01); *C08L 5/12* (2013.01); *C08L 89/06* (2013.01); *C09H 11/00* (2013.01); *C09J 5/00* (2013.01); *C09J 11/06* (2013.01); *C09J 101/28* (2013.01); *C09J 101/286* (2013.01); *C09J 103/02* (2013.01); *C09J 105/00* (2013.01); *C09J 105/04* (2013.01); *C09J 105/06* (2013.01); *C09J 105/12* (2013.01); *C09J 189/005* (2013.01); *C09J 189/06* (2013.01); *D04H 1/413* (2013.01); *D04H 1/4209* (2013.01); *D04H 1/4218* (2013.01); *D04H 1/4266* (2013.01); *D04H 1/587* (2013.01); *D04H 1/593* (2013.01); *D04H 1/64* (2013.01); *D04H 1/724* (2013.01); *D04H 1/74* (2013.01); *D04H 3/002* (2013.01); *D04H 3/004* (2013.01); *E04B 1/74* (2013.01); *E04B 1/80* (2013.01); *E04B 1/88* (2013.01); *E04B 1/94* (2013.01); *E04C 2/284* (2013.01); *E04D 3/352* (2013.01); *E04F 13/0866* (2013.01); *B32B 38/164* (2013.01); *B32B 2037/1215* (2013.01); *B32B 2037/1253* (2013.01); *B32B 2037/1269* (2013.01); *B32B 2250/20* (2013.01); *B32B 2250/40* (2013.01); *B32B 2255/02* (2013.01); *B32B 2255/26* (2013.01); *B32B 2262/108* (2013.01); *B32B 2305/20* (2013.01); *B32B 2305/72* (2013.01); *B32B 2307/304* (2013.01); *B32B 2307/732* (2013.01);
(Continued)

(58) Field of Classification Search
CPC ...... D04H 1/4266; D04H 1/4218; D04H 1/74; D04H 1/413; D04H 1/64; D04H 1/587; D04H 1/724; D04H 1/4209; D04H 1/593; D04H 3/002; D04H 3/004; C09J 101/286; C09J 103/02; C09J 103/04; C09J 105/04; C09J 105/06; C09J 105/12; C09J 105/00; C09J 11/06; C09J 189/06; A01G 24/20; A01G 24/40; A01G 24/15; A01G 24/23; B32B 5/12; B32B 5/26; B32B 7/12; B32B 19/041; B32B 19/04; B32B 15/14; B32B 37/1207; B32B 37/146; B32B 37/12; B32B 37/18; B32B 38/0004; C03C 25/26; C03C 25/32; C03C 25/321; C03C 25/328; C03C 13/06; C08L 5/12; C08L 1/286; C08L 3/02; C08L 89/06; E04B 1/94; E04B 1/88; E04B 1/74; E04B 1/80
USPC ......................................................... 523/217
See application file for complete search history.

(56) References Cited

U.S. PATENT DOCUMENTS 3,411,972 A * 11/1968 Salyer ..................... C08L 89/06
                                                           524/24
3,824,086 A    7/1974 Perry
(Continued)

FOREIGN PATENT DOCUMENTS

CN    101302410 A    11/2008
CN    102068008 A    5/2011
(Continued)

OTHER PUBLICATIONS

J.J. Wilker Nature Chem, Biol. 2011, vol. 7, pp. 579-580.
(Continued)

*Primary Examiner* — Michael M. Bernshteyn
(74) *Attorney, Agent, or Firm* — Abel Schillinger, LLP

(57) ABSTRACT

The invention relates to an aqueous binder composition for mineral fibers comprising at least one polyelectrolytic hydrocolloid.

19 Claims, No Drawings

(51) Int. Cl.

| | |
|---|---|
| C09J 103/02 | (2006.01) |
| C09J 105/04 | (2006.01) |
| C09J 105/06 | (2006.01) |
| C09J 189/06 | (2006.01) |
| D04H 1/4218 | (2012.01) |
| D04H 1/74 | (2006.01) |
| C09J 105/12 | (2006.01) |
| B32B 5/12 | (2006.01) |
| B32B 5/26 | (2006.01) |
| C08L 5/12 | (2006.01) |
| C03C 25/26 | (2018.01) |
| B32B 19/04 | (2006.01) |
| B32B 15/14 | (2006.01) |
| C09J 105/00 | (2006.01) |
| B32B 37/14 | (2006.01) |
| D04H 1/413 | (2012.01) |
| D04H 1/64 | (2012.01) |
| D04H 3/002 | (2012.01) |
| E04B 1/94 | (2006.01) |
| C03C 13/06 | (2006.01) |
| C08L 1/28 | (2006.01) |
| C08L 3/02 | (2006.01) |
| D04H 3/004 | (2012.01) |
| E04B 1/88 | (2006.01) |
| C09J 189/00 | (2006.01) |
| C08J 5/04 | (2006.01) |
| C03C 25/32 | (2018.01) |
| C09J 11/06 | (2006.01) |
| D04H 1/587 | (2012.01) |
| E04B 1/74 | (2006.01) |
| C08L 89/06 | (2006.01) |
| D04H 1/4266 | (2012.01) |
| D04H 1/724 | (2012.01) |
| B32B 7/12 | (2006.01) |
| B32B 37/18 | (2006.01) |
| B32B 38/00 | (2006.01) |
| C03C 25/321 | (2018.01) |
| C03C 25/328 | (2018.01) |
| C09J 5/00 | (2006.01) |
| D04H 1/4209 | (2012.01) |
| D04H 1/593 | (2012.01) |
| E04B 1/80 | (2006.01) |
| E04C 2/284 | (2006.01) |
| E04D 3/35 | (2006.01) |
| E04F 13/08 | (2006.01) |
| E04B 1/76 | (2006.01) |
| C12N 9/06 | (2006.01) |
| C12N 9/02 | (2006.01) |
| C12N 9/08 | (2006.01) |
| C12N 9/10 | (2006.01) |
| C12N 9/90 | (2006.01) |

(52) U.S. Cl.
CPC ....... B32B 2309/02 (2013.01); B32B 2315/14 (2013.01); B32B 2317/00 (2013.01); B32B 2419/06 (2013.01); B32B 2607/00 (2013.01); C03C 2213/00 (2013.01); C03C 2218/11 (2013.01); C08J 2301/28 (2013.01); C08J 2303/02 (2013.01); C08J 2389/06 (2013.01); C08J 2405/00 (2013.01); C08J 2405/04 (2013.01); C08J 2405/06 (2013.01); C08J 2405/12 (2013.01); C08J 2491/00 (2013.01); C08J 2493/00 (2013.01); C08L 2201/52 (2013.01); C08L 2205/03 (2013.01); C09J 2400/146 (2013.01); C09J 2401/00 (2013.01); C09J 2403/00 (2013.01); C09J 2405/00 (2013.01); C09J 2489/00 (2013.01); C12N 9/0022 (2013.01); C12N 9/0051 (2013.01); C12N 9/0059 (2013.01); C12N 9/0065 (2013.01); C12N 9/0071 (2013.01); C12N 9/1044 (2013.01); C12N 9/90 (2013.01); C12Y 104/03013 (2013.01); C12Y 108/03002 (2013.01); C12Y 110/03001 (2013.01); C12Y 111/01007 (2013.01); C12Y 114/18001 (2013.01); C12Y 203/01013 (2013.01); C12Y 203/02013 (2013.01); C12Y 503/04001 (2013.01); D10B 2505/20 (2013.01); E04B 2001/742 (2013.01); E04B 2001/743 (2013.01); E04B 2001/745 (2013.01); E04B 2001/7683 (2013.01)

(56) References Cited

U.S. PATENT DOCUMENTS

| | | | |
|---|---|---|---|
| 4,040,213 A | 8/1977 | Capaul | |
| 4,283,457 A | 8/1981 | Kolsky et al. | |
| 4,552,793 A | 11/1985 | Cameron et al. | |
| 4,613,627 A | 9/1986 | Sherman | |
| 5,218,783 A | 6/1993 | Langezaal | |
| 5,318,990 A | 6/1994 | Strauss | |
| 5,430,070 A * | 7/1995 | Kono | C08J 9/0061 521/70 |
| 10,035,913 B2 * | 7/2018 | Hampson | C09D 197/00 |
| 10,372,051 B2 * | 8/2019 | Varnell | C09D 103/04 |
| 11,124,905 B2 * | 9/2021 | Kiefer | C03C 25/32 |
| 2003/0175335 A1 | 9/2003 | Scott | |
| 2004/0069770 A1 | 4/2004 | Cary et al. | |
| 2006/0165990 A1* | 7/2006 | Curtis | A23P 10/35 428/402.2 |
| 2007/0027283 A1 | 2/2007 | Swift | |
| 2007/0036975 A1* | 2/2007 | Miele | C08K 7/14 427/372.2 |
| 2007/0142596 A1* | 6/2007 | Swift | E04B 1/78 527/312 |
| 2007/0173588 A1 | 7/2007 | Espiard | |
| 2008/0003346 A1 | 1/2008 | Boyer | |
| 2008/0003902 A1 | 1/2008 | Boyer | |
| 2008/0213597 A1 | 9/2008 | Li | |
| 2010/0096580 A1 | 4/2010 | Daschkeit | |
| 2010/0282996 A1 | 11/2010 | Jaffrennou et al. | |
| 2010/0286640 A1 | 11/2010 | Nordby et al. | |
| 2010/0297380 A1 | 11/2010 | Szakola et al. | |
| 2010/0330376 A1 | 12/2010 | Trksak | |
| 2011/0003522 A1 | 1/2011 | Chen | |
| 2011/0021101 A1 | 1/2011 | Hawkins | |
| 2011/0101260 A1 | 5/2011 | Pons Y Moll et al. | |
| 2011/0200814 A1 | 8/2011 | Hernandez-Torres | |
| 2011/0223364 A1 | 9/2011 | Hawkins | |
| 2012/0190262 A1 | 7/2012 | Rosenberg et al. | |
| 2012/0301546 A1* | 11/2012 | Hassan | A23L 33/10 426/103 |
| 2013/0283688 A1 | 10/2013 | Naerum | |
| 2014/0083328 A1 | 3/2014 | Lochel, Jr. | |
| 2014/0148532 A1 | 5/2014 | Omura | |
| 2015/0373924 A1 | 12/2015 | Janssen | |
| 2019/0024303 A1* | 1/2019 | Lee | B32B 7/12 |

FOREIGN PATENT DOCUMENTS

| | | | |
|---|---|---|---|
| CN | 102459320 | A | 5/2012 |
| CN | 103476300 | A | 12/2013 |
| DE | 4130077 | A1 | 3/1993 |
| EA | 014260 | B1 | 12/2008 |
| EA | 017247 | B1 | 2/2010 |
| EA | 019897 | B1 | 12/2010 |
| EP | 0498971 | A1 | 8/1992 |
| EP | 583086 | A | 2/1994 |
| EP | 07081616 | A1 | 4/1996 |
| EP | 0741003 | A1 | 11/1996 |

(56) References Cited

FOREIGN PATENT DOCUMENTS

| | | |
|---|---|---|
| EP | 0058306 A2 | 8/1998 |
| EP | 990727 A1 | 4/2000 |
| EP | 1020198 A2 | 7/2000 |
| EP | 1184033 A1 | 3/2002 |
| EP | 1741726 A1 | 1/2007 |
| EP | 2246312 A2 | 11/2010 |
| EP | 2424886 B1 | 4/2013 |
| EP | 2738232 A1 | 6/2014 |
| EP | 2990494 A1 | 3/2016 |
| ES | 1074717 U | 6/2011 |
| FR | 2307858 A1 | 11/1976 |
| GB | 849833 A | 9/1960 |
| GB | 926749 A | 5/1963 |
| GB | 1215113 A1 | 12/1970 |
| NL | 1001508 C2 | 5/1997 |
| RU | 2017770 C1 | 8/1994 |
| RU | 2325419 C1 | 2/2008 |
| RU | 2448830 C2 | 10/2011 |
| RU | 2488606 C2 | 1/2012 |
| RU | 2501825 C2 | 5/2012 |
| SU | 431139 A | 6/1974 |
| WO | 8303092 A1 | 3/1983 |
| WO | 8807614 A1 | 10/1988 |
| WO | 9210602 A1 | 6/1992 |
| WO | 9318642 A1 | 9/1993 |
| WO | 9508259 A1 | 3/1995 |
| WO | 9719141 A1 | 5/1997 |
| WO | 9720780 A1 | 6/1997 |
| WO | 9936368 A1 | 7/1999 |
| WO | 9951536 A1 | 10/1999 |
| WO | 0017121 A1 | 3/2000 |
| WO | 0105725 A1 | 1/2001 |
| WO | 0159026 A2 | 8/2001 |
| WO | 0187070 A1 | 11/2001 |
| WO | 0196460 A1 | 12/2001 |
| WO | 0206178 A1 | 1/2002 |
| WO | 2004007615 A1 | 1/2004 |
| WO | 2005068574 A1 | 7/2005 |
| WO | 2006061249 A1 | 6/2006 |
| WO | 2007014236 A2 | 2/2007 |
| WO | 2008005635 A2 | 1/2008 |
| WO | 2008023032 A1 | 2/2008 |
| WO | 2009080696 A2 | 7/2009 |
| WO | 2009080938 A2 | 7/2009 |
| WO | 2010106181 A1 | 9/2010 |
| WO | 2010125163 A1 | 11/2010 |
| WO | 2010132641 A1 | 11/2010 |
| WO | 2011012712 A1 | 2/2011 |
| WO | 2011138458 A1 | 11/2011 |
| WO | 2012013780 A1 | 2/2012 |
| WO | 2012028650 A1 | 3/2012 |
| WO | 2012118939 A1 | 9/2012 |
| WO | 2012166414 A1 | 12/2012 |
| WO | 2014135681 A1 | 9/2014 |
| WO | 2016005481 A1 | 1/2016 |
| WO | 2016102444 A1 | 6/2016 |
| WO | 2017051106 A1 | 3/2017 |

OTHER PUBLICATIONS

Sartuqui Javier et al: "Biomimetic fiber mesh scaffolds based on gelatin and hydroxyapatite nano-rods: Designing intrinsic skills to attain bone reparation abilities".Colloids and Surfaces. B. Biointerfaces. Elsevier. Amsterdam. NL. vol. 145. May 9, 2016 (May 9, 2016). pp. 382-391.

Emmett P. Broderick, Damien M. O'halloran, Yury A. Rochev, Martin Griffin,Russell J. Collighan, Abhay S. Pandit: "Enzymatic stabilization of gelatin-based scaffolds". Journal of Medical Materials Research, vol. 72B, No. 1, Oct. 15, 2004 (Oct. 15, 2004). pp. 37-42.

Irina G Plashchina et al: "Phase behavior of gelatin in the presence of pectin in water-acid medium". Polymer Bulletin, Springer, Berlin, DE. vol. 58, No. 3, Oct. 13, 2006 (Oct. 13, 2006), pp. 587-596.

Bae H J et al: "Effects of transglutaminase-induced cross-linking on properties of fish gelatin-nanoclay composite film", Food Chemistry, Elsevier Ltd. NL, vol. 114, No. 1, May 1, 2009 (May 1, 2009), pp. 180-189.

V. Zitko, J. Rosik: "Reakcia Pektinu so Zelatinou Zlozenie Komplexov Pektinu a Gelatiny", Chemicke Zvesti, vol. XVI, No. 6, Oct. 30, 1961 (Oct. 30, 1961), pp. 474-481.

C. Pena, K. de la Caba, A. Eceiza, R. Ruseckaite, I. Mondragon in Biores. Technol. 2010, 101, pp. 6836-6842.

Ma, Wen et al., "Characterization of gelatin-based edible films incorporated with olive oil", Food Research International, 49 (2012), pp. 572-579.

\* cited by examiner

BINDER COMPOSITION

FIELD OF THE INVENTION

The present invention relates to an aqueous binder composition for mineral fibres, a mineral wool product bound with a binder, a method of producing a mineral wool product bound with a binder, and the use of at least one polyelectrolytic hydrocolloid in a binder composition for the production of a mineral wool product.

BACKGROUND OF THE INVENTION

Mineral fibre products generally comprise man-made vitreous fibres (MMVF) such as, e.g., glass fibres, ceramic fibres, basalt fibres, slag wool, mineral wool and stone wool, which are bonded together by a cured thermoset polymeric binder material. For use as thermal or acoustical insulation products, bonded mineral fibre mats are generally produced by converting a melt made of suitable raw materials to fibres in conventional manner, for instance by a spinning cup process or by a cascade rotor process. The fibres are blown into a forming chamber and, while airborne and while still hot, are sprayed with a binder solution and randomly deposited as a mat or web onto a travelling conveyor. The fibre mat is then transferred to a curing oven where heated air is blown through the mat to cure the binder and rigidly bond the mineral fibres together.

In the past, the binder resins of choice have been phenol-formaldehyde resins which can be economically produced and can be extended with urea prior to use as a binder. However, the existing and proposed legislation directed to the lowering or elimination of formaldehyde emissions have led to the development of formaldehyde-free binders such as, for instance, the binder compositions based on polycarboxy polymers and polyols or polyamines, such as disclosed in EP-A-583086, EP-A-990727, EP-A-1741726, U.S. Pat. No. 5,318,990 and US-A-2007/0173588.

Another group of non-phenol-formaldehyde binders are the addition/-elimination reaction products of aliphatic and/or aromatic anhydrides with alkanolamines, e.g., as disclosed in WO 99/36368, WO 01/05725, WO 01/96460, WO 02/06178, WO 2004/007615 and WO 2006/061249. These binder compositions are water soluble and exhibit excellent binding properties in terms of curing speed and curing density. WO 2008/023032 discloses urea-modified binders of that type which provide mineral wool products having reduced moisture take-up.

Since some of the starting materials used in the production of these binders are rather expensive chemicals, there is an ongoing need to provide formaldehyde-free binders which are economically produced.

A further effect in connection with previously known aqueous binder compositions from mineral fibres is that at least the majority of the starting materials used for the productions of these binders stem from fossil fuels. There is an ongoing trend of consumers to prefer products that are fully or at least partly produced from renewable materials and there is therefore a need to provide binders for mineral wool which are at least partly produced from renewable materials.

A further effect in connection with previously known aqueous binder compositions for mineral fibres is that they involve components which are corrosive and/or harmful. This requires protective measures for the machinery involved in the production of mineral wool products to prevent corrosion and also requires safety measures for the persons handling this machinery. This leads to increased costs and health issues and there is therefore a need to provide binder compositions for mineral fibres with a reduced content of corrosive and/or harmful materials.

A yet further effect in connection with previously known aqueous binder compositions from mineral fibres is that these binders are conventionally associated with extensive curing equipment for curing the binder. The curing equipment is conventionally an oven operating at temperatures far above 100° C. such as around 200° C. Binder compositions curable under these conditions are termed thermoset binder compositions. The oven is several meters long to accommodate the web that is continuously fed into the oven and to ensure that the web is fully cured when leaving the oven. Such oven equipment is associated with extensive energy consumption.

The reference EP 2424886 B1 (Dynea OY) describes a composite material comprising a crosslinkable resin of a proteinous material. In a typical embodiment, the composite material is a cast mould comprising an inorganic filler, like e.g. sand, and/or wood, and a proteinous material as well as enzymes suitable for crosslinking the proteinous material. A mineral wool product is not described in EP 2424886 B1.

The reference C. Pea, K. de la Caba, A. Eceiza, R. Ruseckaite, I. Mondragon in Biores. Technol. 2010, 101, 6836-6842 is concerned with the replacement of non-biodegradable plastic films by renewable raw materials from plants and wastes of meat industry. In this connection, this reference describes the use of hydrolysable chestnut-tree tannin for modification of a gelatine in order to form films. The reference does not describe binders, in particular not binders for mineral wool.

SUMMARY OF THE INVENTION

Accordingly, it was an object of the present invention to provide a binder composition which is particularly suitable for bonding mineral fibres, uses renewable materials as starting materials, reduces or eliminates corrosive and/or harmful materials.

Further, it was an object of the present invention to provide a binder composition which does not require high temperature for curing and therefore eliminates need of high temperature to be applied in the production of a product bonded with the binder.

A further object of the present invention was to provide a mineral wool product bonded with such a binder composition.

A further object of the present invention was to provide a method of making such a mineral wool product.

A further object of the present invention was to provide the use of such a binder composition for the preparation of a mineral wool product.

A further object of the present invention was to provide a method of bonding together the surfaces of two or more elements, whereby at least one of the two or more elements is a mineral wool element, whereby the method uses an adhesive that does not require high temperatures for curing and whereby during the handling, application, and curing of the adhesive exposure to harmful substances is minimized and no protective measures are necessary.

In accordance with a first aspect of the present invention, there is provided a, preferably formaldehyde-free, binder composition for mineral fibres comprising at least one polyelectrolytic hydrocolloid.

In accordance with a second aspect of the present invention, there is provided a mineral wool product comprising mineral fibres bound by a binder resulting from the curing of a binder composition comprising at least one polyelectrolytic hydrocolloid.

In accordance with a third aspect of the present invention, there is provided a method of producing a mineral wool product which comprises the steps of contacting mineral fibres with a binder composition comprising at least one polyelectrolytic hydrocolloid.

In accordance with a fourth aspect of the present invention, there is provided the use of a polyelectrolytic hydrocolloid in a binder for the production of a mineral wool product.

In accordance with a fifth aspect of the present invention, there is provided a method of bonding together the surfaces of two or more elements, whereby at least one of the two or more elements is a mineral wool element, said elements being bound by a mineral wool binder, the method comprising the steps of:

providing two or more elements,
applying an adhesive to one or more of the surfaces to be bonded together before, during or after contacting the surfaces to be bonded together with each other,
curing the adhesive, wherein the adhesive comprises,
at least one polyelectrolytic hydrocolloid.

The present inventors have surprisingly found that it is possible to obtain a mineral wool product comprising mineral fibres bound by a binder resulting from the curing of a binder composition, whereby the binder composition can be produced from renewable materials to a large degree, does not contain, or contains only to a minor degree, any corrosive and/or harmful agents and the production of the mineral wool product does not lead to pollution such as VOC's (Volatile Organic Compounds) during the preparation.

The present inventors have also surprisingly found that it is possible to bond together the surfaces of mineral wool elements with each other or of one or more mineral wool element with another element by using the method described.

DESCRIPTION OF THE PREFERRED EMBODIMENTS

A binder composition according to the present invention comprises at least one polyelectrolytic hydrocolloid.

In a preferred embodiment, the binders according to the present invention are formaldehyde free.

For the purpose of the present application, the term "formaldehyde free" is defined to characterize a mineral wool product where the emission is below 5 $\mu g/m^2/h$ of formaldehyde from the mineral wool product, preferably below 3 $\mu g/m^2/h$. Preferably, the test is carried out in accordance with ISO 16000 for testing aldehyde emissions.

A surprising advantage of embodiments of mineral wool products according to the present invention is that they show self-healing properties. After being exposed to very harsh conditions when mineral wool products loose a part of their strength, the mineral wool products according to the present invention can regain a part of, the whole of or even exceed the original strength. In one embodiment, the aged strength is at least 80%, such as at least 90%, such as at least 100%, such as at least 130%, such as at least 150% of the unaged strength. This is in contrast to conventional mineral wool products for which the loss of strength after being exposed to harsh environmental conditions is irreversible. While not wanting to be bound to any particular theory, the present inventors believe that this surprising property in mineral wool products according to the present invention is due to the complex nature of the bonds formed in the network of the cured binder composition, such as the protein crosslinked by the phenol and/or quinone containing compound or crosslinked by an enzyme, which also includes quaternary structures and hydrogen bonds and allows bonds in the network to be established after returning to normal environmental conditions. For an insulation product, which when e.g. used as a roof insulation can be exposed to very high temperatures in the summer, this is an important advantage for the long term stability of the product.

Polyelectrolytic Hydrocolloid

Hydrocolloids are hydrophilic polymers, of vegetable, animal, microbial or synthetic origin, that generally contain many hydroxyl groups and may be polyelectrolytes. They are widely used to control the functional properties of aqueous foodstuffs.

Hydrocolloids may be proteins or polysaccharides and are fully or partially soluble in water and are used principally to increase the viscosity of the continuous phase (aqueous phase) i.e. as gelling agent or thickener. They can also be used as emulsifiers since their stabilizing effect on emulsions derives from an increase in viscosity of the aqueous phase.

A hydrocolloid usually consists of mixtures of similar, but not identical molecules and arising from different sources and methods of preparation. The thermal processing and for example, salt content, pH and temperature all affect the physical properties they exhibit. Descriptions of hydrocolloids often present idealised structures but since they are natural products (or derivatives) with structures determined by for example stochastic enzymatic action, not laid down exactly by the genetic code, the structure may vary from the idealised structure.

Many hydrocolloids are polyelectrolytes (for example alginate, gelatine, carboxymethylcellulose and xanthan gum).

Polyelectrolytes are polymers where a significant number of the repeating units bear an electrolyte group. Polycations and polyanions are polyelectrolytes. These groups dissociate in aqueous solutions (water), making the polymers charged. Polyelectrolyte properties are thus similar to both electrolytes (salts) and polymers (high molecular weight compounds) and are sometimes called polysalts.

The charged groups ensure strong hydration, particularly on a per-molecule basis. The presence of counterions and co-ions (ions with the same charge as the polyelectrolyte) introduce complex behavior that is ion-specific.

A proportion of the counterions remain tightly associated with the polyelectrolyte, being trapped in its electrostatic field and so reducing their activity and mobility.

In one embodiment the binder composition comprise one or more counter-ion(s) selected from the group of Mg2+, Ca2+, Sr2+, Ba2+.

Another property of a polyelectrolyte is the high linear charge density (number of charged groups per unit length).

Generally neutral hydrocolloids are less soluble whereas polyelectrolytes are more soluble.

Many hydrocolloids also gel. Gels are liquid-water-containing networks showing solid-like behavior with characteristic strength, dependent on their concentration, and hardness and brittleness dependent on the structure of the hydrocolloid(s) present.

Hydrogels are hydrophilic crosslinked polymers that are capable of swelling to absorb and hold vast amounts of water. They are particularly known from their use in sanitary products. Commonly used materials make use of polyacrylates, but hydrogels may be made by crosslinking soluble hydrocolloids to make an insoluble but elastic and hydrophilic polymer.

Examples of hydrocolloids comprise: Agar agar, Alginate, Arabinoxylan, Carrageenan, Carboxymethylcellulose, Cellulose, Curdlan, Gelatine, Gellan, β-Glucan, Guar gum, Gum arabic, Locust bean gum, Pectin, Starch, Xanthan gum.

In one embodiment, the at least one polyelectrolytic hydrocolloid is selected from the group consisting of gelatine, pectin, alginate, carrageenan, gum arabic, xanthan gum, cellulose derivatives such as carboxymethylcellulose.

In one embodiment, the at least one polyelectrolytic hydrocolloid is a gel former.

In one embodiment, the at least one polyelectrolytic hydrocolloid is used in form of a salt, such as a salt of Na+, K+, NH4+, Mg2+, Ca2+, Sr2+, Ba2+.

Gelatine

Gelatine is derived from chemical degradation of collagen. Gelatine is water soluble and has a molecular weight of 10.000 to 500.000 g/mol, such as 30.000 to 300.000 g/mol dependent on the grade of hydrolysis. Gelatine is a widely used food product and it is therefore generally accepted that this compound is totally non-toxic and therefore no precautions are to be taken when handling gelatine.

Gelatine is a heterogeneous mixture of single or multi-stranded polypeptides, typically showing helix structures. Specifically, the triple helix of type I collagen extracted from skin and bones, as a source for gelatine, is composed of two α1(I) and one α2(I) chains.

Gelatine solutions may undergo coil-helix transitions.

A type gelatins are produced by acidic treatment. B type gelatines are produced by basic treatment.

Chemical cross-links may be introduced to gelatine. In one embodiment, transglutaminase is used to link lysine to glutamine residues; in one embodiment, glutaraldehyde is used to link lysine to lysine, in one embodiment, tannins are used to link lysine residues.

The gelatine can also be further hydrolysed to smaller fragments of down to 3000 g/mol.

On cooling a gelatine solution, collagen like helices may be formed.

Other hydrocolloids may also comprise helix structures such as collagen like helices. Gelatine may form helix structures.

In one embodiment, the cured binder comprising polyelectrolytic hydrocolloid comprises helix structures.

In one embodiment, the at least one polyelectrolytic hydrocolloid is a low strength gelatine, such as a gelatine having a gel strength of 30 to 125 Bloom.

In one embodiment, the at least one polyelectrolytic hydrocolloid is a medium strength gelatine, such as a gelatine having a gel strength of 125 to 180 Bloom.

In one embodiment, the at least one polyelectrolytic hydrocolloid is a high strength gelatine, such as a gelatine having a gel strength of 180 to 300 Bloom.

In a preferred embodiment, the gelatine is preferably originating from one or more sources from the group consisting of mammal, bird species, such as from cow, pig, horse, fowl, and/or from scales, skin of fish.

In one embodiment, urea may be added to the binder compositions according to the present invention. The inventors have found that the addition of even small amounts of urea causes denaturation of the gelatin, which can slow down the gelling, which might be desired in some embodiments. The addition of urea might also lead to a softening of the product.

The inventors have found that the carboxylic acid groups in gelatins interact strongly with trivalent and tetravalent ions, for example aluminium salts. This is especially true for type B gelatines which contain more carboxylic acid groups than type A gelatines.

The present inventors have found that in some embodiments, curing/drying of binder compositions according to the present invention including gelatin should not start off at very high temperatures.

The inventors have found that starting the curing at low temperatures may lead to stronger products. Without being bound to any particular theory, it is assumed by the inventors that starting curing at high temperatures may lead to an impenetrable outer shell of the binder composition which hinders water from underneath to get out.

Surprisingly, the binders according to the present invention including gelatines are very heat resistant. The present inventors have found that in some embodiments the cured binders can sustain temperatures up to 300° C. without degradation.

Pectin

Pectin is a heterogeneous grouping of acidic structural polysaccharides, found in fruit and vegetables which form acid-stable gels.

Generally, pectins do not possess exact structures, instead it may contain up to 17 different monosaccharides and over 20 types of different linkages. D-galacturonic acid residues form most of the molecules.

Gel strength increases with increasing Ca2+ concentration but reduces with temperature and acidity increase (pH<3).

Pectin may form helix structures.

The gelling ability of the di-cations is similar to that found with alginates (Mg2+ is much less than for Ca2+, Sr2+ being less than for Ba2+).

Alginate

Alginates are scaffolding polysaccharides produced by brown seaweeds.

Alginates are linear unbranched polymers containing β-(1,4)-linked D-mannuronic acid (M) and α-(1,4)-linked L-guluronic acid (G) residues. Alginate may also be a bacterial alginate, such as which are additionally O-acetylated. Alginates are not random copolymers but, according to the source algae, consist of blocks of similar and strictly alternating residues (that is, MMMMMM, GGGGGG and GMGMGMGM), each of which have different conformational preferences and behavior. Alginates may be prepared with a wide range of average molecular weights (50-100000 residues). The free carboxylic acids have a water molecule H3O+ firmly hydrogen bound to carboxylate. Ca2+ ions can replace this hydrogen bonding, zipping guluronate, but not mannuronate, chains together stoichiometrically in a so-called egg-box like conformation. Recombinant epimerases with different specificities may be used to produce designer alginates.

Alginate may form helix structures.

Carrageenan

Carrageenan is a collective term for scaffolding polysaccharides prepared by alkaline extraction (and modification) from red seaweed.

Carrageenans are linear polymers of about 25,000 galactose derivatives with regular but imprecise structures, dependent on the source and extraction conditions.

κ-carrageenan (kappa-carrageenan) is produced by alkaline elimination from μ-carrageenan isolated mostly from the tropical seaweed *Kappaphycus alvarezii* (also known as *Eucheuma cottonii*).

ι-carrageenan (iota-carrageenan) is produced by alkaline elimination from ν-carrageenan isolated mostly from the Philippines seaweed *Eucheuma denticulatum* (also called *Spinosum*).

λ-carrageenan (lambda-carrageenan) (isolated mainly from *Gigartina pistillata* or *Chondrus crispus*) is converted into ε-carrageenan (theta-carrageenan) by alkaline elimination, but at a much slower rate than causes the production of ι-carrageenan and κ-carrageenan.

The strongest gels of κ-carrageenan are formed with K+ rather than Li+, Na+, Mg2+, Ca2+, or Sr2+.

All carrageenans may form helix structures.

Gum Arabic

Gum arabic is a complex and variable mixture of arabinogalactan oligosaccharides, polysaccharides and glycoproteins. Gum arabic consists of a mixture of lower relative molecular mass polysaccharide and higher molecular weight hydroxyproline-rich glycoprotein with a wide variability.

Gum arabic has a simultaneous presence of hydrophilic carbohydrate and hydrophobic protein.

Xanthan Gum

Xanthan gum is a microbial desiccation-resistant polymer prepared e.g. by aerobic submerged fermentation from *Xanthomonas campestris*.

Xanthan gum is an anionic polyelectrolyte with a β-(1, 4)-D-glucopyranose glucan (as cellulose) backbone with side chains of -(3,1)-α-linked D-mannopyranose-(2,1)-β-D-glucuronic acid-(4,1)-β-D-mannopyranose on alternating residues.

Xanthan gums natural state has been proposed to be bimolecular antiparallel double helices. A conversion between the ordered double helical conformation and the single more-flexible extended chain may take place at between 40° C.-80° C. Xanthan gums may form helix structures.

Xanthan gums may contain cellulose.

Cellulose Derivatives

An example of a polyelectrolytic cellulose derivative is carboxymethylcellulose.

Carboxymethylcellulose (CMC) is a chemically modified derivative of cellulose formed by its reaction with alkali and chloroacetic acid.

The CMC structure is based on the β-(1,4)-D-glucopyranose polymer of cellulose. Different preparations may have different degrees of substitution, but it is generally in the range 0.6-0.95 derivatives per monomer unit.

In a preferred embodiment, the binder composition comprises at least two polyelectrolytic hydrocolloids, wherein one polyelectrolytic hydrocolloid is gelatine and the at least one other polyelectrolytic hydrocolloid is selected from the group consisting of pectin, alginate, carrageenan, gum arabic, xanthan gum, cellulose derivatives such as carboxymethylcellulose.

In one embodiment, the binder composition comprises at least two polyelectrolytic hydrocolloids, wherein one polyelectrolytic hydrocolloid is gelatine and the at least other polyelectrolytic hydrocolloid is pectin.

In one embodiment, the binder composition comprises at least two polyelectrolytic hydrocolloids, wherein one polyelectrolytic hydrocolloid is gelatine and the at least other polyelectrolytic hydrocolloid is alginate.

In one embodiment, the binder composition comprises at least two polyelectrolytic hydrocolloids, wherein one polyelectrolytic hydrocolloid is gelatine and the at least other polyelectrolytic hydrocolloid is carboxymethylcellulose.

In a preferred embodiment, the binder composition according to the present invention comprises at least two polyelectrolytic hydrocolloids, wherein one polyelectrolytic hydrocolloid is gelatine and wherein the gelatine is present in the aqueous binder composition in an amount of 10 to 95 wt.-%, such as 20 to 80 wt.-%, such as 30 to 70 wt.-%, such as 40 to 60 wt.-%, based on the weight of the polyelectrolytic hydrocolloids.

In one embodiment, the binder composition comprises at least two polyelectrolytic hydrocolloids, wherein the one polyelectrolytic hydrocolloid and the at least other polyelectrolytic hydrocolloid have complementary charges.

In one embodiment, the one polyelectrolytic hydrocolloid is one or more of gelatine or gum arabic having complementary charges from one or more polyelectrolytic hydrocolloid(s) selected from the group of pectin, alginate, carrageenan, xanthan gum or carboxymethylcellulose.

In one embodiment, the binder composition is capable of curing at a temperature of not more than 95° C., such as 5-95° C., such as 10-80° C., such as 20-60° C., such as 40-50° C.

In one embodiment, the aqueous binder composition according to the present invention is not a thermoset binder.

A thermosetting composition is in a soft solid or viscous liquid state, preferably comprising a prepolymer, preferably comprising a resin, that changes irreversibly into an infusible, insoluble polymer network by curing.[1] Curing is typically induced by the action of heat, whereby typically temperatures above 95° C. are needed.

A cured thermosetting resin is called a thermoset or a thermosetting plastic/polymer—when used as the bulk material in a polymer composite, they are referred to as the thermoset polymer matrix.

In one embodiment, the aqueous binder composition according to the present invention does not contain a poly(meth)acrylic acid, a salt of a poly(meth)acrylic acid or an ester of a poly(meth)acrylic acid.

In one embodiment, the at least one polyelectrolytic hydrocolloid is a biopolymer or modified biopolymer.

Biopolymers are polymers produced by living organisms. Biopolymers may contain monomeric units that are covalently bonded to form larger structures.

There are three main classes of biopolymers, classified according to the monomeric units used and the structure of the biopolymer formed: Polynucleotides (RNA and DNA), which are long polymers composed of 13 or more nucleotide monomers; Polypeptides, such as proteins, which are polymers of amino acids; Polysaccharides, such as linearly bonded polymeric carbohydrate structures.

Polysaccharides may be linear or branched; they are typically joined with glycosidic bonds. In addition, many saccharide units can undergo various chemical modifications, and may form parts of other molecules, such as glycoproteins.

In one embodiment, the at least one polyelectrolytic hydrocolloid is a biopolymer or modified biopolymer with a polydispersity index regarding molecular mass distribution of 1, such as 0.9 to 1.

In one embodiment, the binder composition comprises proteins from animal sources, including collagen, gelatine, and hydrolysed gelatine, and the binder composition further comprises at least one phenol and/or quinone containing compound, such as tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, the binder composition comprises proteins from animal sources, including collagen, gelatine, and hydrolysed gelatine, and wherein the binder composition further comprises at least one enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

In one embodiment, the binder composition comprises gelatine, and the binder composition further comprises a tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups, preferably tannic acid.

In one embodiment, the binder composition comprises gelatine, and the binder composition further comprises at least one enzyme which is a transglutaminase (EC 2.3.2.13).

In one embodiment, the aqueous binder composition is formaldehyde-free.

In one embodiment, the binder composition according to the present invention is consisting essentially of:
at least one polyelectrolytic hydrocolloid;
optionally at least one oil;
optionally at least one pH-adjuster;
optionally at least one crosslinker;
optionally at least one anti-fouling agent;
optionally at least one anti-swelling agent;
water.

In one embodiment, the at least one oil is a non-emulsified hydrocarbon oil. In one embodiment, the at least one oil is an emulsified hydrocarbon oil. In one embodiment, the at least one oil is a plant-based oil.

In one embodiment, the at least one crosslinker is tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, the at least one crosslinker is an enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

In one embodiment, the at least one anti-swelling agent is tannic acid and/or tannins.

In one embodiment, the at least one anti-fouling agent is an antimicrobial agent.

Antimicrobial agents may be benzoic acid, propionic acid, sodium benzoate, sorbic acid, and potassium sorbate to inhibit the outgrowth of both bacterial and fungal cells. However, natural biopreservatives may be used. Chitosan is regarded as being antifungal and antibacterial. The most frequently used biopreservatives for antimicrobial are lysozyme and nisin. Common other biopreservatives that may be used are bacteriocins, such as lacticin and pediocin and antimicrobial enzymes, such as chitinase and glucose oxidase. Also, the use of the enzyme lactoperoxidase (LPS) presents antifungal and antiviral activities. Natural antimicrobial agents may also be used, such as tannins, rosemary, and garlic essential oils, oregano, lemon grass, or cinnamon oil at different concentrations.

Mineral Wool Product

The present invention is also directed to a mineral wool product comprising mineral fibers bound by a binder as described above.

In one embodiment, the loss on ignition (LOI) of the mineral wool product according to the present invention is within the range of 0.1 to 25.0%, such as 0.3 to 18.0%, such as 0.5 to 12.0%, such as 0.7 to 8.0% by weight.

In one embodiment, the binder is not crosslinked.

In an alternative embodiment, the binder is crosslinked.

The present invention is also directed to a mineral wool product comprising a mineral wool product comprising mineral fibers bound by a binder resulting from the curing of a binder composition comprising a polyelectrolytic hydrocolloid.

In one embodiment, the binder results from the curing of a binder composition in which the at least one polyelectrolytic hydrocolloid is selected from the group consisting of gelatin, pectin, alginate, carrageenan, gum arabic, xanthan gum, cellulose derivatives such as carboxymethylcellulose.

In one embodiment, the binder results from the curing of a binder composition comprising at least two polyelectrolytic hydrocolloids, wherein one polyelectrolytic hydrocolloid is gelatine and the at least one other polyelectrolytic hydrocolloid is selected from the group consisting of pectin, alginate, carrageenan, gum arabic, xanthan gum, cellulose derivatives such as carboxymethylcellulose.

In one embodiment, the binder results from the curing of a binder composition in which the gelatine is present in an amount of 10 to 95 wt.-%, such as 20 to 80 wt.-%, such as 30 to 70 wt.-%, such as 40 to 60 wt.-%, based on the weight of the polyelectrolytic hydrocolloids.

In one embodiment, the binder results from the curing of a binder composition in which the one polyelectrolytic hydrocolloid and the at least other polyelectrolytic hydrocolloid have complementary charges.

In one embodiment, the loss on ignition (LOI) is within the range of 0.1 to 25.0%, such as 0.3 to 18.0%, such as 0.5 to 12.0%, such as 0.7 to 8.0% by weight.

In one embodiment, the binder results from the curing of a binder composition at a temperature of less than 95° C., such as 5-95° C., such as 10-80° C., such as 20-60° C., such as 40-50° C.

In one embodiment, the binder results from the curing of a binder composition which is not a thermoset binder composition.

In one embodiment, the binder results from a binder composition which does not contain a poly(meth)acrylic acid, a salt of a poly(meth)acrylic acid or an ester of a poly(meth)acrylic acid.

In one embodiment, the binder results from the curing of a binder composition comprising at least one polyelectrolytic hydrocolloid which is a biopolymer or modified biopolymer.

In one embodiment, the binder results from the curing of a binder composition comprising proteins from animal sources, including collagen, gelatine, and hydrolysed gelatine, and the binder composition further comprises at least one phenol and/or quinone containing compound, such as tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, the binder results from the curing of a binder composition comprising proteins from animal sources, including collagen, gelatine, and hydrolysed gelatine, and wherein the binder composition further comprises at least one enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

In one embodiment, the binder results from the curing of a binder composition comprising gelatine, and wherein the binder composition further comprises a tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups, preferably tannic acid.

In one embodiment, the binder results from the curing of a binder composition comprising gelatine, and wherein the binder composition further comprises at least one enzyme which is a transglutaminase (EC 2.3.2.13)

In one embodiment, the binder results from the curing of a binder composition which is formaldehyde-free.

In one embodiment, the binder results from a binder composition consisting essentially of
at least one polyelectrolytic hydrocolloid;
optionally at least one oil;
optionally at least one pH-adjuster;
optionally at least one crosslinker;
optionally at least one anti-fouling agent;
optionally at least one anti-swelling agent;
water.

In one embodiment, the binder is not crosslinked.
In one embodiment, the binder is crosslinked.
Reaction of the Binder Components The present inventors have found that in some embodiments of the mineral wool product according to the present invention are best to be produced when the binder is applied to the mineral fibres under acidic conditions. Therefore, in a preferred embodiment, the binder applied to the mineral fibres comprises a pH-adjuster, in particular in form of a pH buffer.

In a preferred embodiment, the binder in its uncured state has a pH value of less than 8, such as less than 7, such as less than 6.

The present inventors have found that in some embodiments, the curing of the binder is strongly accelerated under alkaline conditions. Therefore, in one embodiment, the binder composition for mineral fibres comprises a pH-adjuster, preferably in form of a base, such as organic base, such as amine or salts thereof, inorganic bases, such as metal hydroxide, such as KOH or NaOH, ammonia or salts thereof.

In a particular preferred embodiment, the pH adjuster is an alkaline metal hydroxide, in particular NaOH.

In a preferred embodiment, the binder composition according to the present invention has a pH of 7 to 10, such as 7.5 to 9.5, such as 8 to 9.

Other additives may be components such as one or more reactive or nonreactive silicones and may be added to the binder. Preferably, the one or more reactive or nonreactive silicone is selected from the group consisting of silicone constituted of a main chain composed of organosiloxane residues, especially diphenylsiloxane residues, alkylsiloxane residues, preferably dimethylsiloxane residues, bearing at least one hydroxyl, acyl, carboxyl or anhydride, amine, epoxy or vinyl functional group capable of reacting with at least one of the constituents of the binder composition and is preferably present in an amount of 0.1-15 weight-%, preferably from 0.1-10 weight-%, more preferably 0.3-8 weight-%, based on the total binder mass.

In one embodiment, an oil may be added to the binder composition.

In one embodiment, the at least one oil is a non-emulsified hydrocarbon oil. In one embodiment, the at least one oil is an emulsified hydrocarbon oil. In one embodiment, the at least one oil is a plant-based oil.

In one embodiment, the at least one crosslinker is tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, the at least one crosslinker is an enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

In one embodiment, the at least one anti-swelling agent is tannic acid and/or tannins.

In one embodiment, the at least one anti-fouling agent is an antimicrobial agent.

Antimicrobial agents may be benzoic acid, propionic acid, sodium benzoate, sorbic acid, and potassium sorbate to inhibit the outgrowth of both bacterial and fungal cells. However, natural biopreservatives may be used. Chitosan is regarded as being antifungal and antibacterial. The most frequently used biopreservatives for antimicrobial are lysozyme and nisin. Common other biopreservatives that may be used are bacteriocins, such as lacticin and pediocin and antimicrobial enzymes, such as chitinase and glucose oxidase. Also, the use of the enzyme lactoperoxidase (LPS) presents antifungal and antiviral activities. Natural antimicrobial agents may also be used, such as tannins, rosemary, and garlic essential oils, oregano, lemon grass, or cinnamon oil at different concentrations.

In one embodiment, an anti-fouling agent may be added to the binder.

In a preferred embodiment, the anti-fouling agent is a tannin, in particular a tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, an anti-swelling agent may be added to the binder, such as tannic acid and/or tannins.

Further additives may be additives containing calcium ions and antioxidants.

In one embodiment, the binder composition according to the present invention contains additives in form of linkers containing acyl groups and/or amine groups and/or thiol groups. These linkers can strengthen and/or modify the network of the cured binder.

In one embodiment, the binder compositions according to the present invention contain further additives in form of additives selected from the group consisting of PEG-type reagents, silanes, and hydroxylapatites.

Properties of the Mineral Wool Product

In a preferred embodiment, the density of the mineral wool product is in the range of 10-1200 kg/m$^3$, such as 30-800 kg/m$^3$, such as 40-600 kg/m$^3$, such as 50-250 kg/m$^3$, such as 60-200 kg/m$^3$.

In a preferred embodiment, the mineral wool product according to the present invention is an insulation product, in particular having a density of 10 to 200 kg/m$^3$.

Method of Producing a Mineral Wool Product

The present invention also provides a method for producing a mineral wool product by binding mineral fibres with the binder composition.

Accordingly, the present invention is also directed to a method for producing a mineral wool product which comprises the steps of contacting mineral fibers with a binder composition comprising at least one polyelectrolytic hydrocolloid, and curing the binder.

In one embodiment, the at least one polyelectrolytic hydrocolloid is selected from the group consisting of gelatin, pectin, alginate, carrageenan, gum arabic, xanthan gum, cellulose derivatives such as carboxymethylcellulose.

In one embodiment, the binder composition comprises at least two polyelectrolytic hydrocolloids, wherein one polyelectrolytic hydrocolloid is gelatine and the at least one other polyelectrolytic hydrocolloid is selected from the group consisting of pectin, alginate, carrageenan, gum arabic, xanthan gum, cellulose derivatives such as carboxymethylcellulose.

In one embodiment, the gelatine is present in the aqueous binder composition in an amount of 10 to 95 wt.-%, such as 20 to 80 wt.-%, such as 30 to 70 wt.-%, such as 40 to 60 wt.-%, based on the weight of the polyelectrolytic hydrocolloids.

In one embodiment, the one polyelectrolytic hydrocolloid and the at least other polyelectrolytic hydrocolloid have complementary charges.

In one embodiment, the at least one polyelectrolytic hydrocolloid is present in the aqueous binder composition in an amount of 1 to 50, such as 2.5 to 25 wt.-%, based on the weight of the aqueous binder composition.

In one embodiment, the step of curing the binder composition takes place at a temperature of not more than 95° C., such as 5-95° C., such as 10-80° C., such as 20-60° C., such as 40-50° C.

In one embodiment, the binder composition is not a thermoset binder.

In one embodiment, the binder composition does not contain a poly(meth)acrylic acid, a salt of a poly(meth)acrylic acid or an ester of a poly(meth)acrylic acid.

In one embodiment, the at least one polyelectrolytic hydrocolloid is a biopolymer or modified biopolymer.

In one embodiment, the binder composition comprises proteins from animal sources, including collagen, gelatine, and hydrolysed gelatine, and the binder composition further comprises at least one phenol and/or quinone containing compound, such as tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, the binder composition comprises proteins from animal sources, including collagen, gelatine, and hydrolysed gelatine, and wherein the binder composition further comprises at least one enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

In one embodiment, the binder composition is formaldehyde-free.

In one embodiment, the binder composition is consisting essentially of
at least one polyelectrolytic hydrocolloid;
optionally at least one oil;
optionally at least one pH-adjuster;
optionally at least one crosslinker;
optionally at least one anti-fouling agent;
optionally at least one anti-swelling agent;
water.

In one embodiment, the method does not involve crosslinking of the binder.

In one embodiment, the method does involve crosslinking of the binder.

In one embodiment, the at least one oil is a non-emulsified hydrocarbon oil. In one embodiment, the at least one oil is an emulsified hydrocarbon oil. In one embodiment, the at least one oil is a plant-based oil.

In one embodiment, the at least one crosslinker is tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, the at least one crosslinker is an enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

In one embodiment, the binder composition comprises gelatine, and the binder composition further comprises a tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups, preferably tannic acid.

In one embodiment, the binder composition comprises gelatine, and the binder composition further comprises at least one enzyme which is a transglutaminase (EC 2.3.2.13).

In one embodiment, the at least one anti-swelling agent is tannic acid and/or tannins.

In one embodiment, the at least one anti-fouling agent is an antimicrobial agent.

Antimicrobial agents may be benzoic acid, propionic acid, sodium benzoate, sorbic acid, and potassium sorbate to inhibit the outgrowth of both bacterial and fungal cells. However, natural biopreservatives may be used. Chitosan is regarded as being antifungal and antibacterial. The most frequently used biopreservatives for antimicrobial are lysozyme and nisin. Common other biopreservatives that may be used are bacteriocins, such as lacticin and pediocin and antimicrobial enzymes, such as chitinase and glucose oxidase. Also, the use of the enzyme lactoperoxidase (LPS) presents antifungal and antiviral activities. Natural antimicrobial agents may also be used, such as tannins, rosemary, and garlic essential oils, oregano, lemon grass, or cinnamon oil at different concentrations.

In one embodiment, the curing process comprises a drying process, in particular by blowing air or gas over/through the mineral wool product or by increasing temperature.

The present invention is also directed to a mineral wool product prepared by a method as described above.

Preferably, the mineral wool product prepared by such a use has a loss on ignition (LOI) within the range of 0.1 to 25.0%, such as 0.3 to 18.0%, such as 0.5 to 12.0%, such as 0.7 to 8.0% by weight.

A particular advantage of the mineral wool product according to the present invention is that it does not require high temperatures for curing. This does not only save energy, reduces VOC and obviates the need for machinery to be highly temperature resistant, but also allows for a high flexibility in a process for the production of mineral wool products with these binders.

In one embodiment the method comprises the steps of:
making a melt of raw materials,
fibrerising the melt by means of a fiber forming apparatus to form mineral fibres,
providing the mineral fibres in the form of a collected web,
mixing the binder with the mineral fibres before, during or after the provision of the collected web to form a mixture of mineral fibres and binder,
curing the mixture of mineral fibres and binder.

In one embodiment, the binder is supplied in the close vicinity of the fibre forming apparatus, such as a cup spinning apparatus or a cascade spinning apparatus, in either case immediately after the fibre formation. The fibres with applied binder are thereafter conveyed onto a conveyor belt as a web.

The web may be subjected to longitudinal or length compression after the fibre formation and before substantial curing has taken place.

Fiber Forming Apparatus

There are various types of centrifugal spinners for fiberising mineral melts.

A conventional centrifugal spinner is a cascade spinner which comprises a sequence of a top (or first) rotor and a subsequent (or second) rotor and optionally other subsequent rotors (such as third and fourth rotors). Each rotor rotates about a different substantially horizontal axis with a rotational direction opposite to the rotational direction of the or each adjacent rotor in the sequence. The different horizontal axes are arranged such that melt which is poured on to the top rotor is thrown in sequence on to the peripheral surface of the or each subsequent rotor, and fibres are thrown off the or each subsequent rotor, and optionally also off the top rotor.

In one embodiment, a cascade spinner or other spinner is arranged to fiberise the melt and the fibres are entrained in air as a cloud of the fibres.

Many fiber forming apparatuses comprise a disc or cup that spins around a substantially, vertical axis. It is then conventional to arrange several of these spinners in-line, i.e. substantially in the first direction, for instance as described in GB-A-926,749, U.S. Pat. No. 3,824,086 and WO-A-83/03092.

There is usually a stream of air associated with the one or each fiberising rotor whereby the fibres are entrained in this air as they are formed off the surface of the rotor.

In one embodiment, binder and/or additives is added to the cloud of fibres by known means. The amount of binder and/or additive may be the same for each spinner or it may be different.

In one embodiment, a hydrocarbon oil may be added into the cloud of fibres.

As used herein, the term "collected web" is intended to include any mineral fibres that have been collected together on a surface, i.e. they are no longer entrained in air, e.g. the fibrerised mineral fibres, granulate, tufts or recycled web waste. The collected web could be a primary web that has been formed by collection of fibres on a conveyor belt and provided as a starting material without having been crosslapped or otherwise consolidated.

Alternatively, the collected web could be a secondary web that has been formed by crosslapping or otherwise consolidating a primary web. Preferably, the collected web is a primary web.

In one embodiment the mixing of the binder with the mineral fibres is done after the provision of the collected web in the following steps:
subjecting the collected web of mineral fibres to a disentanglement process,
suspending the mineral fibres in a primary air flow,
mixing binder composition with the mineral fibres before, during or after the disentanglement process to form a mixture of mineral fibres and binder.

A method of producing a mineral wool product comprising the process step of disentanglement is described in EP10190521.

In one embodiment, the disentanglement process comprises feeding the collected web of mineral fibres from a duct with a lower relative air flow to a duct with a higher relative air flow. In this embodiment, the disentanglement is believed to occur, because the fibres that enter the duct with the higher relative air flow first are dragged away from the subsequent fibres in the web. This type of disentanglement is particularly effective for producing open tufts of fibres, rather than the compacted lumps that can result in an uneven distribution of materials in the product.

According to a particularly preferred embodiment, the disentanglement process comprises feeding the collected web to at least one roller which rotates about its longitudinal axis and has spikes protruding from its circumferential surface. In this embodiment, the rotating roller will usually also contribute at least in part to the higher relative air flow. Often, rotation of the roller is the sole source of the higher relative air flow.

In preferred embodiments, the mineral fibres and optionally the binder are fed to the roller from above. It is also preferred for the disentangled mineral fibres and optionally the binder to be thrown away from the roller laterally from the lower part of its circumference. In the most preferred embodiment, the mineral fibres are carried approximately 180 degrees by the roller before being thrown off.

The binder may be mixed with the mineral fibres before, during or after the disentanglement process. In some embodiments, it is preferred to mix the binder with the fibres prior to the disentanglement process. In particular, the fibres can be in the form of an uncured collected web containing binder.

It is also feasible that the binder be pre-mixed with a collected web of mineral fibres before the disentanglement process. Further mixing could occur during and after the disentanglement process. Alternatively, it could be supplied to the primary air flow separately and mixed in the primary air flow.

The mixture of mineral fibres and binder is collected from the primary air flow by any suitable means. In one embodiment, the primary air flow is directed into the top of a cyclone chamber, which is open at its lower end and the mixture is collected from the lower end of the cyclone chamber.

The mixture of mineral fibres and binder is preferably thrown from the disentanglement process into a forming chamber.

Having undergone the disentanglement process, the mixture of mineral fibres and binder is collected, pressed and cured. Preferably, the mixture is collected on a foraminous conveyor belt having suction means positioned below it.

In a preferred method according to the invention, the mixture of binder and mineral fibres, having been collected, is pressed and cured.

In a preferred method according to the invention, the mixture of binder and mineral fibres, having been collected, is scalped before being pressed and cured.

The method may be performed as a batch process, however according to an embodiment the method is performed at a mineral wool production line feeding a primary or secondary mineral wool web into the fibre separating process, which provides a particularly cost efficient and versatile method to provide composites having favourable mechanical properties and thermal insulation properties in a wide range of densities.

At the same time, because of the curing at ambient temperature, the likelihood of uncured binder spots is strongly decreased.

Curing

The web is cured by a chemical and/or physical reaction of the binder components.

In one embodiment, the curing takes place in a curing device.

In one embodiment the curing is carried out at temperatures from 5 to 95° C., such as 5 to 80° C., such as 5 to 60° C., such as 8 to 50° C., such as 10 to 40° C.

In one embodiment the curing takes place in a conventional curing oven for mineral wool production operating at a temperature of from 5 to 95° C., such as 5 to 80° C., such as 10 to 60° C., such as 20 to 40° C.

The curing process may commence immediately after application of the binder to the fibres. The curing is defined as a process whereby the binder composition undergoes a physical and/or chemical reaction which in case of a chemical reaction usually increases the molecular weight of the compounds in the binder composition and thereby increases the viscosity of the binder composition, usually until the binder composition reaches a solid state.

In one embodiment the curing process comprises crosslinking and/or water inclusion as crystal water.

In one embodiment the cured binder contains crystal water that may decrease in content and raise in content depending on the prevailing conditions of temperature, pressure and humidity.

In one embodiment the curing process comprises a drying process.

In a preferred embodiment, the curing of the binder in contact with the mineral fibers takes place in a heat press.

The curing of a binder in contact with the mineral fibers in a heat press has the particular advantage that it enables the production of high-density products.

In one embodiment the curing process comprises drying by pressure. The pressure may be applied by blowing air or gas through/over the mixture of mineral fibres and binder. The blowing process may be accompanied by heating or cooling or it may be at ambient temperature.

In one embodiment the curing process takes place in a humid environment.

The humid environment may have a relative humidity RH of 60-99%, such as 70-95%, such as 80-92%. The curing in a humid environment may be followed by curing or drying to obtain a state of the prevalent humidity.

In one embodiment the curing is performed in oxygen-depleted surroundings.

Without wanting to be bound by any particular theory, the applicant believes that performing the curing in an oxygen-depleted surrounding is particularly beneficial when the binder composition includes an enzyme because it increases the stability of the enzyme component in some embodiments, in particular of the transglutaminase enzyme, and thereby improves the crosslinking efficiency. In one embodiment, the curing process is therefore performed in an inert atmosphere, in particular in an atmosphere of an inert gas, like nitrogen.

In some embodiments, in particular in embodiments in which the binder composition includes phenolics, in particular tannins oxidizing agents can be added. Oxidising agents as additives can serve to increase the oxidising rate of the phenolics in particular tannins. One example is the enzyme tyrosinase which oxidizes phenols to hydroxyphenols/quinones and therefore accelerates the binder forming reaction.

In another embodiment, the oxidising agent is oxygen, which is supplied to the binder.

In one embodiment, the curing is performed in oxygen-enriched surroundings.

The mineral wool product can be in any conventional configuration, for instance a mat or slab, and can be cut and/or shaped (e.g. into pipe sections) before, during or after curing of the binder.

Use of a Polyelectrolytic Hydrocolloid in a Binder Composition

The present invention is also directed to the use of at least one polyelectrolytic hydrocolloid in a binder composition for the production of a mineral wool product.

In one embodiment, the at least one polyelectrolytic hydrocolloid is selected from the group consisting of gelatin, pectin, alginate, carrageenan, gum arabic, xanthan gum, cellulose derivatives such as carboxymethylcellulose.

In one embodiment, at least two polyelectrolytic hydrocolloids are used, wherein one polyelectrolytic hydrocolloid is gelatine and the at least one other polyelectrolytic hydrocolloid is selected from the group consisting of pectin, alginate, carrageenan, gum arabic, xanthan gum, cellulose derivatives such as ca rboxymethylcellulose.

In one embodiment, the gelatine is used in an amount of 10 to 95 wt.-%, such as 20 to 80 wt.-%, such as 30 to 70 wt.-%, such as 40 to 60 wt.-%, based on the weight of the polyelectrolytic hydrocolloids.

In one embodiment, the one polyelectrolytic hydrocolloid and the at least other polyelectrolytic hydrocolloid have complementary charges.

In one embodiment, the at least one polyelectrolytic hydrocolloid is used in an aqueous binder composition for a mineral wool product in an amount of 1 to 50, such as 2.5 to 15 wt.-%, based on the weight of the aqueous binder composition.

In one embodiment, the curing of the aqueous binder composition for the production of a mineral wool product takes place at a temperature of not more than 95° C., such as 5-95° C., such as 10-80° C., such as 20-60° C., such as 40-50° C.

In one embodiment, at least one polyelectrolytic hydrocolloid is used in an aqueous binder composition for the production of a mineral wool product which is not a thermoset binder.

In one embodiment, the polyelectrolytic hydrocolloid is used in a binder for the production of the mineral wool product which does not contain a poly(meth)acrylic acid, a salt of a poly(meth)acrylic acid or an ester of a poly(meth)acrylic acid.

In one embodiment, the at least one polyelectrolytic hydrocolloid is a biopolymer or modified biopolymer.

In one embodiment, the binder composition comprises proteins from animal sources, including collagen, gelatine, and hydrolysed gelatine, and the binder composition further comprises at least one phenol and/or quinone containing compound, such as tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, the binder composition comprises proteins from animal sources, including collagen, gelatine, and hydrolysed gelatine, and wherein the binder composition further comprises at least one enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

In one embodiment, the binder composition comprises gelatine, and wherein the binder composition further comprises a tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups, preferably tannic acid.

In one embodiment, the binder composition comprises gelatine, and wherein the binder composition further comprises at least one enzyme which is a transglutaminase (EC 2.3.2.13).

In one embodiment, the at least one polyelectrolytic hydrocolloid is used in a binder for the production of a mineral wool product which is formaldehyde-free.

In one embodiment, the at least one polyelectrolytic hydrocolloid is used in an aqueous binder composition for the production of a mineral wool product consisting essentially of:
- at least one polyelectrolytic hydrocolloid;
- optionally at least one oil;
- optionally at least one pH-adjuster;
- optionally at least one crosslinker;
- optionally at least one anti-fouling agent;
- optionally at least one anti-swelling agent;
- water.

In one embodiment, the use does not involve a crosslinking of the binder composition.

In one embodiment, the use does involve a crosslinking of the binder composition.

In one embodiment, the at least one oil is a non-emulsified hydrocarbon oil. In one embodiment, the at least one oil is an emulsified hydrocarbon oil. In one embodiment, the at least one oil is a plant-based oil.

In one embodiment, the at least one crosslinker is tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, the at least one crosslinker is an enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

In one embodiment, the at least one anti-swelling agent is tannic acid and/or tannins.

In one embodiment, the at least one anti-fouling agent is an antimicrobial agent.

Antimicrobial agents may be benzoic acid, propionic acid, sodium benzoate, sorbic acid, and potassium sorbate to inhibit the outgrowth of both bacterial and fungal cells. However, natural biopreservatives may be used. Chitosan is regarded as being antifungal and antibacterial. The most frequently used biopreservatives for antimicrobial are lysozyme and nisin. Common other biopreservatives that may be used are bacteriocins, such as lacticin and pediocin and antimicrobial enzymes, such as chitinase and glucose oxidase. Also, the use of the enzyme lactoperoxidase (LPS) presents antifungal and antiviral activities. Natural antimicrobial agents may also be used, such as tannins, rosemary, and garlic essential oils, oregano, lemon grass, or cinnamon oil at different concentrations.

The present invention is also directed to a mineral wool product prepared by the use as described above.

Preferably, the mineral wool product prepared by such a use has a loss on ignition (LOI) in the range of 0.1 to 25.0%, such as 0.3 to 18.0%, such as 0.5 to 12.0%, such as 0.7 to 8.0% by weight.

Advantages of the Binder Composition

The mineral wool product according to the present invention has the surprising advantage that it can be produced by a very simple binder which requires as little as only one component, namely at least one polyelectrolytic hydrocolloid, whereby no pre-reaction of this binder is necessary. The mineral wool product according to the present invention is therefore produced from natural and non-toxic components and is therefore safe to work with. At the same time, the mineral wool product according to the present invention is produced from a binder based on renewable resources.

Because the binder used for the production of the mineral wool product according to the present invention can be cured at ambient temperature or in the vicinity of ambient temperature, the energy consumption during the production of the products is very low. The non-toxic and non-corrosive nature of embodiments of the binders in combination with the curing at ambient temperatures allows a much less complex machinery to be involved. At the same time, because of the curing at ambient temperature, the likelihood of uncured binder spots is strongly decreased.

Further important advantages are the self-repair capacities of mineral wool products produced from the binders.

A further advantage of the mineral wool products is that they may be shaped as desired after application of the binder but prior to curing. This opens the possibility for making tailor-made products, like pipe sections.

A further advantage is the strongly reduced punking risk. Punking may be associated with exothermic reactions during manufacturing of the mineral wool product which increase temperatures through the thickness of the insulation causing a fusing or devitrification of the mineral fibres and eventually creating a fire hazard. In the worst case, punking causes fires in the stacked pallets stored in warehouses or during transportation.

Yet another advantage is the absence of emissions during curing, in particular the absence of VOC emissions.

Method of Bonding Together the Surfaces of Two or More Elements

The present inventors have surprisingly found that the composition described above can also serve as an adhesive in a method for bonding together surfaces of two or more elements.

Accordingly, the present invention is also directed to a method of bonding together surfaces of two or more elements, whereby at least one of the two or more elements is a mineral wool element, said mineral wool element(s) being bound by a mineral wool binder, the method comprising the steps of:
providing two or more elements,
applying an adhesive to one or more of the surfaces to be bonded together before, during or after contacting the surfaces to be bonded together with each other,
curing the adhesive, wherein the adhesive comprises,
at least one polyelectrolytic hydrocolloid.

In one embodiment, two or more elements are two or more mineral wool elements.

In one embodiment, the two or more elements comprise at least one element, which is not a mineral wool element.

In one embodiment, the at least one element, which is not a mineral wool element, is selected from the group consisting of a fleece, such as a glass fibre fleece, a building structure such as a wall, a ceiling, a roof.

In one embodiment, the at least one polyelectrolytic hydrocolloid is selected from the group consisting of gelatine, pectin, alginate, carrageenan, gum arabic, xanthan gum, cellulose derivatives such as carboxymethylcellulose.

In one embodiment, the adhesive comprises at least two polyelectrolytic hydrocolloids, wherein one polyelectrolytic hydrocolloid is gelatine and the at least one other polyelectrolytic hydrocolloid is selected from the group consisting of pectin, alginate, carrageenan, gum arabic, xanthan gum, cellulose derivatives such as carboxymethylcellulose.

In one embodiment, the gelatine is present in the adhesive an amount of 10 to 95 wt.-%, such as 20 to 80 wt.-%, such as 30 to 70 wt.-%, such as 40 to 60 wt.-%, based on the weight of the polyelectrolytic hydrocolloids.

In one embodiment, the one polyelectrolytic hydrocolloid and the at least other polyelectrolytic hydrocolloid have complementary charges.

In one embodiment, the adhesive is capable of curing at a temperature of not more than 95° C., such as 5-95° C., such as 10-80° C., such as 20-60° C., such as 40-50° C.

In one embodiment, the adhesive is not a thermoset adhesive.

In one embodiment, the adhesive does not contain a poly(meth)acrylic acid, a salt of a poly(meth)acrylic acid or an ester of a poly(meth)acrylic acid.

In one embodiment, the at least one polyelectrolytic hydrocolloid is a biopolymer or modified biopolymer.

In one embodiment, the adhesive comprises proteins from animal sources, including collagen, gelatine and hydrolysed gelatine, and the adhesive further comprises at least one phenol and/or quinone containing compound, such as tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, the adhesive comprises proteins from animal sources, including collagen, gelatine and hydrolysed gelatine, and wherein the adhesive further comprises at least one enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

In one embodiment, the adhesive comprises gelatine, and the adhesive further comprises a tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups, preferably tannic acid.

In one embodiment, the adhesive comprises gelatine, and the adhesive further comprises at least one enzyme which is a transglutaminase (EC 2.3.2.13).

In one embodiment, the adhesive is formaldehyde-free.

In one embodiment, the adhesive consists essentially of
at least one polyelectrolytic hydrocolloid;
optionally at least one oil;
optionally at least one pH-adjuster;
optionally at least one crosslinker;
optionally at least one anti-fouling agent;
optionally at least one anti-swelling agent;
water.

In one embodiment, the at least one oil is a non-emulsified hydrocarbon oil.

In one embodiment, the at least one oil is an emulsified hydrocarbon oil.

In one embodiment, the at least one oil is a plant-based oil.

In one embodiment, the at least one crosslinker is tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, the at least one crosslinker is an enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

In one embodiment, the at least one anti-swelling agent is tannic acid and/or tannins.

In one embodiment, the at least one anti-fouling agent is an antimicrobial agent.

Antimicrobial agents may be benzoic acid, propionic acid, sodium benzoate, sorbic acid, and potassium sorbate to inhibit the outgrowth of both bacterial and fungal cells. However, natural biopreservatives may be used. Chitosan is regarded as being antifungal and antibacterial. The most frequently used biopreservatives for antimicrobial are lysozyme and nisin. Common other biopreservatives that may be used are bacteriocins, such as lacticin and pediocin and antimicrobial enzymes, such as chitinase and glucose oxidase. Also, the use of the enzyme lactoperoxidase (LPS) presents antifungal and antiviral activities. Natural antimicrobial agents may also be used, such as tannins, rosemary, and garlic essential oils, oregano, lemon grass, or cinnamon oil at different concentrations.

The present inventors have surprisingly found that it is possible to bond together the surfaces of mineral wool elements with each other of one or more wool elements with another element by using the method described. Since the adhesive used for the method in some embodiments does usually not contain any harmful substances and does usually not set free any harmful substances during the curing, the method can be carried out by any person on-site of use without any protective measures and without a need for specific training for the person to carry out the method.

EXAMPLES

In the following examples, several binders which fall under the definition of the present invention were prepared and compared to binders according to the prior art.

Binders According to the Prior Art

The following properties were determined for the binders according the prior art.

Reagents

Silane (Momentive VS-142) was supplied by Momentive and was calculated as 100% for simplicity. All other components were supplied in high purity by Sigma-Aldrich and were assumed anhydrous for simplicity unless stated otherwise.

Binder Component Solids Content—Definition

The content of each of the components in a given binder solution before curing is based on the anhydrous mass of the components. The following formula can be used:

$$\text{Binder component solids content } (\%) = \\ \frac{\text{binder component } A \text{ solids } (g) + \text{binder component } B \text{ solids } (g) + \ldots}{\text{total weight of mixture } (g)} \times 100\%$$

Binder Solids—Definition and Procedure

The content of binder after curing is termed "binder solids".

Disc-shaped stone wool samples (diameter: 5 cm; height 1 cm) were cut out of stone wool and heat-treated at 580° C. for at least 30 minutes to remove all organics. The solids of the binder mixture (see below for mixing examples) were measured by distributing a sample of the binder mixture (approx. 2 g) onto a heat treated stone wool disc in a tin foil container. The weight of the tin foil container containing the stone wool disc was weighed before and directly after addition of the binder mixture. Two such binder mixture loaded stone wool discs in tin foil containers were produced and they were then heated at 200° C. for 1 hour. After cooling and storing at room temperature for 10 minutes, the samples were weighed and the binder solids were calculated as an average of the two results. A binder with the desired binder solids could then be produced by diluting with the required amount of water and 10% aq. silane (Momentive VS-142).

Reaction Loss—Definition

The reaction loss is defined as the difference between the binder component solids content and the binder solids.

Mechanical Strength Studies (Bar Tests)—Procedure

The mechanical strength of the binders was tested in a bar test. For each binder, 16 bars were manufactured from a mixture of the binder and stone wool shots from the stone wool spinning production. The shots are particles which have the same melt composition as the stone wool fibers, and the shots are normally considered a waste product from the spinning process. The shots used for the bar composition have a size of 0.25-0.50 mm.

A 15% binder solids binder solution containing 0.5% silane (Momentive VS-142) of binder solids was obtained as described above under "binder solids". A sample of this binder solution (16.0 g) was mixed well with shots (80.0 g). The resulting mixture was then divided evenly into four slots in a heat resistant silicone form for making small bars (4×5 slots per form; slot top dimension: length=5.6 cm, width=2.5 cm; slot bottom dimension: length=5.3 cm, width=2.2 cm; slot height=1.1 cm). The mixtures placed in the slots were then pressed hard with a suitably sized flat metal bar to generate even bar surfaces. 16 bars from each binder were made in this fashion. The resulting bars were then cured at 200° C. for 1 h. After cooling to room temperature, the bars were carefully taken out of the containers. Eight of the 16 bars were aged in an autoclave (15 min/120° C./1.2 bar).

After drying for 1-2 days, all bars were then broken in a 3 point bending test (test speed: 10.0 mm/min; rupture level: 50%; nominal strength: 30 N/mm$^2$; support distance: 40 mm; max deflection 20 mm; nominal e-module 10000 N/mm$^2$) on a Bent Tram machine to investigate their mechanical strengths. The bars were placed with the "top face" up (i.e. the face with the dimensions length=5.6 cm, width=2.5 cm) in the machine.

Loss of Ignition (LOI) of Bars

The loss of ignition (LOI) of bars was measured in small tin foil containers by treatment at 580° C. For each measurement, a tin foil container was first heat-treated at 580° C. for 15 minutes to remove all organics. The tin foil container was allowed to cool to ambient temperature, and was then weighed. Four bars (usually after being broken in the 3 point bending test) were placed into the tin foil container and the ensemble was weighed. The tin foil container containing bars was then heat-treated at 580° C. for 30 minutes, allowed to cool to ambient temperature, and finally weighed again. The LOI was then calculated using the following formula:

$$LOI\ (\%) = \frac{\text{Weight of bars before heat treatment (g)} - \text{Weight of bars after heat treatment (g)}}{\text{Weight of bars before heat treatment (g)}} \times 100\%$$

Reference Binders from the Prior Art Prepared as Comparative Examples

Binder example, reference binder A (phenol-formaldehyde resin modified with urea, a PUF-resol)

A phenol-formaldehyde resin is prepared by reacting 37% aq. formaldehyde (606 g) and phenol (189 g) in the presence of 46% aq. potassium hydroxide (25.5 g) at a reaction temperature of 84° C. preceded by a heating rate of approximately 1° C. per minute. The reaction is continued at 84° C. until the acid tolerance of the resin is 4 and most of the phenol is converted. Urea (241 g) is then added and the mixture is cooled.

The acid tolerance (AT) expresses the number of times a given volume of a binder can be diluted with acid without the mixture becoming cloudy (the binder precipitates). Sulfuric acid is used to determine the stop criterion in a binder production and an acid tolerance lower than 4 indicates the end of the binder reaction. To measure the AT, a titrant is produced from diluting 2.5 mL conc. sulfuric acid (>99%) with 1 L ion exchanged water. 5 mL of the binder to be investigated is then titrated at room temperature with this titrant while keeping the binder in motion by manually shaking it; if preferred, use a magnetic stirrer and a magnetic stick. Titration is continued until a slight cloud appears in the binder, which does not disappear when the binder is shaken.

The acid tolerance (AT) is calculated by dividing the amount of acid used for the titration (mL) with the amount of sample (mL):

AT=(Used titration volume (mL))/(Sample volume (mL))

Using the urea-modified phenol-formaldehyde resin obtained, a binder is made by addition of 25% aq. ammonia (90 mL) and ammonium sulfate (13.2 g) followed by water (1.30 kg). The binder solids were then measured as described above and the mixture was diluted with the required amount of water and silane (Momentive VS-142) for mechanical strength studies (15% binder solids solution, 0.5% silane of binder solids).

Binders According to the Present Invention

The following properties were determined for the binders according the present invention.

Reagents

Gelatines (Speisegelatine, type A, porcine, 120 and 180 bloom; Imagel LB, type B, 122 bloom) were obtained from Gelita AG. Tannorouge chestnut tree tannin was obtained from Brouwland bvba. Agar agar (05039), gellan gum (P8169), pectin from citrus peel (P9135), sodium alginate from brown algae (A0682), sodium carboxymethyl cellulose (419303), soluble starch (S9765), and sodium hydroxide were obtained from Sigma-Aldrich. For simplicity, these reagents were considered completely pure and anhydrous.

Binder Component Solids Content—Definition

The content of each of the components in a given binder solution before curing is based on the anhydrous mass of the components. The following formula can be used:

$$\text{Binder component solids content (\%)} = \frac{\text{binder component } A \text{ solids (g)} + \text{binder component } B \text{ solids (g)} + \ldots}{\text{total weight of mixture (g)}} \times 100\%$$

Mechanical Strength Studies (Bar Tests)—Procedure

The mechanical strength of the binders was tested in a bar test. For each binder, 8-16 bars were manufactured from a mixture of the binder and stone wool shots from the stone wool spinning production. The shots are particles which have the same melt composition as the stone wool fibers, and the shots are normally considered a waste product from the spinning process. The shots used for the bar composition have a size of 0.25-0.50 mm.

A binder solution was obtained as described in the examples below. For comparatively slower setting binders, a sample of the binder solution (16.0 g for binders with 10-15% binder component solids; 32.0 g for binders with 5% binder component solids) was mixed well with shots (80.0 g). The resulting mixture was then divided evenly into four slots in a heat resistant silicone form for making small bars (4×5 slots per form; slot top dimension: length=5.6 cm, width=2.5 cm; slot bottom dimension: length=5.3 cm, width=2.2 cm; slot height=1.1 cm). For comparatively faster setting binders, a sample of the binder solution (8.0 g for binders with 10-15% binder component solids and 16.0 g for binders with 5% binder component solids) was mixed well with shots (40.0 g, pre-heated to 35-40° C. before use), and the resulting mixture was then divided evenly into two slots only. During the manufacture of each bar, the mixtures placed in the slots were pressed as required and then evened out with a plastic spatula to generate an even bar surface. 8-16 bars from each binder were made in this fashion. The resulting bars were then cured at room temperature for 1-2 days or first cured for 15 minutes in an oven at the temperatures listed in the tables followed by curing for 1-2 days at room temperature. If still not sufficiently cured after that time, the bars were cured for 1 day at 35° C. The bars were then carefully taken out of the containers, turned upside down and left for a day at room temperature to cure completely. Half of the 8-16 bars were aged in an autoclave (15 min/120° C./1.2 bar).

After drying for 1-2 days, all bars were then broken in a 3 point bending test (test speed: 10.0 mm/min; rupture level: 50%; nominal strength: 30 N/mm$^2$; support distance: 40 mm; max deflection 20 mm; nominal e-module 10000 N/mm$^2$) on a Bent Tram machine to investigate their mechanical strengths. The bars were placed with the "top face" up (i.e. the face with the dimensions length=5.6 cm, width=2.5 cm) in the machine.

Loss of Ignition (LOI) of Bars

The loss of ignition (LOI) of bars was measured in small tin foil containers by treatment at 580° C. For each measurement, a tin foil container was first heat-treated at 580° C. for 15 minutes to remove all organics. The tin foil container was allowed to cool to ambient temperature, and was then weighed. Four bars (usually after being broken in the 3 point bending test) were placed into the tin foil container and the ensemble was weighed. The tin foil container containing bars was then heat-treated at 580° C. for 30 minutes, allowed to cool to ambient temperature, and finally weighed again. The LOI was then calculated using the following formula:

$$LOI\ (\%) = \frac{\text{Weight of bars before heat treatment (g)} - \text{Weight of bars after heat treatment (g)}}{\text{Weight of bars before heat treatment (g)}} \times 100\%$$

Binder Compositions According to the Present Invention

Binder Example, Entry 1

A mixture of gelatine (Speisegelatine, type A, porcine, 120 bloom, 7.5 g) in water (42.5 g) was stirred at 50° C. for approx. 15-30 min until a clear solution was obtained (pH 5.1). The resulting solution was then used in the subsequent experiments.

Binder Example, Entry 3

A mixture of gelatine (Speisegelatine, type A, porcine, 180 bloom, 8.82 g) in water (50.0 g) was stirred at 50° C. for approx. 15-30 min until a clear solution was obtained (pH 5.2). The resulting solution was then used in the subsequent experiments.

Binder Example, Entry 5

A mixture of gelatine (Imagel LB, type B, 122 bloom, 8.82 g) in water (50.0 g) was stirred at 50° C. for approx. 15-30 min until a clear solution was obtained (pH 5.1). The resulting solution was then used in the subsequent experiments.

Binder Example, Entry 7

To water (50.0 g) stirred vigorously at 85° C. was added sodium carboxymethyl cellulose (2.63 g) portion-wise over approx. 15 minutes. Stirring was continued for 0.5-1 h further at 85° C. until a clear solution was obtained (pH 8.4). The resulting solution was then used in the subsequent experiments.

Binder Example, Entry 8

To water (50.0 g) stirred vigorously at 85° C. was added agar agar (2.63 g) portion-wise over approx. 15 minutes. Stirring was continued for 0.5-1 h further at 85° C. until a clear solution was obtained.

A mixture of gelatine (Speisegelatine, type A, porcine, 120 bloom, 8.82 g) in water (50.0 g) was stirred at 50° C. for approx. 15-30 min until a clear solution was obtained. A portion of the above agar agar solution (19.6 g, thus efficiently 0.98 g agar agar and 18.6 g water) was then added and stirring was continued at 50° C. for 5 min further (pH 5.3). The resulting solution was then used in the subsequent experiments.

Binder Example, Entry 9

To water (50.0 g) stirred vigorously at 85° C. was added gellan gum (2.63 g) portion-wise over approx. 15 minutes. Stirring was continued for 0.5-1 h further at 85° C. until a clear solution was obtained.

A mixture of gelatine (Speisegelatine, type A, porcine, 120 bloom, 8.82 g) in water (50.0 g) was stirred at 50° C. for approx. 15-30 min until a clear solution was obtained. A portion of the above gellan gum solution (19.6 g, thus efficiently 0.98 g gellan gum and 18.6 g water) was then added and stirring was continued at 50° C. for 5 min further (pH 5.3). The resulting solution was then used in the subsequent experiments.

Binder Example, Entry 10

To water (50.0 g) stirred vigorously at 85° C. was added pectin (2.63 g) portion-wise over approx. 15 minutes. Stirring was continued for 0.5-1 h further at 85° C. until a clear solution was obtained.

A mixture of gelatine (Speisegelatine, type A, porcine, 120 bloom, 8.82 g) in water (50.0 g) was stirred at 50° C. for approx. 15-30 min until a clear solution was obtained. A portion of the above pectin solution (19.6 g, thus efficiently 0.98 g pectin and 18.6 g water) was then added and stirring was continued at 50° C. for 5 min further (pH 4.8). The resulting solution was then used in the subsequent experiments.

Binder Example, Entry 11

To water (50.0 g) stirred vigorously at 85° C. was added sodium alginate (2.63 g) portion-wise over approx. 15 minutes. Stirring was continued for 0.5-1 h further at 85° C. until a clear solution was obtained.

A mixture of gelatine (Speisegelatine, type A, porcine, 120 bloom, 8.82 g) in water (50.0 g) was stirred at 50° C. for approx. 15-30 min until a clear solution was obtained. A portion of the above sodium alginate solution (19.6 g, thus efficiently 0.98 g sodium alginate and 18.6 g water) was then added and stirring was continued at 50° C. for 5 min further (pH 5.3). The resulting solution was then used in the subsequent experiments.

Binder Example, Entry 12

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 8.00 g) in water (72.0 g) was stirred at 50° C. for approx. 15-30 min until a clear solution was obtained (pH 4.8). 1M NaOH (3.50 g) was then added (pH 9.3) followed by a portion of the above chestnut tree tannin solution (3.60 g; thus efficiently 0.80 g chestnut tree tannin). After stirring for 1-2 minutes further at 50° C., the resulting brown mixture (pH 9.2) was used in the subsequent experiments.

Binder Example, Entry 13

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 10.0 g) in water (56.7 g) was stirred at 50° C. for approx. 15-30 min until a clear solution was obtained (pH 4.9). 1M NaOH (4.00 g) was then added (pH 9.1) followed by a portion of the above chestnut tree tannin solution (4.50 g; thus efficiently 1.00 g chestnut tree tannin). After stirring for 1-2 minutes further at 50° C., the resulting brown mixture (pH 9.1) was used in the subsequent experiments.

Binder Example, Entry 16

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 180 bloom, 10.0 g) in water (56.7 g) was stirred at 50° C. for approx. 15-30 min until a clear solution was obtained (pH 4.8). 1M NaOH (3.50 g) was then added (pH 9.2) followed by a portion of the above chestnut tree tannin solution (4.50 g; thus efficiently 1.00 g chestnut tree tannin). After stirring for 1-2 minutes further at 50° C., the resulting brown mixture (pH 9.2) was used in the subsequent experiments.

Binder Example, Entry 18

To 1M NaOH (15.75 g) stirred at room temperature was added chestnut tree tannin (4.50 g). Stirring was continued at room temperature for 5-10 min further, yielding a deep red-brown solution.

A mixture of gelatine (Imagel LB, type B, 122 bloom, 10.0 g) in water (56.7 g) was stirred at 50° C. for approx. 15-30 min until a clear solution was obtained (pH 4.7). 1M NaOH (3.50 g) was then added (pH 9.2) followed by a portion of the above chestnut tree tannin solution (4.50 g; thus efficiently 1.00 g chestnut tree tannin). After stirring for 1-2 minutes further at 50° C., the resulting brown mixture (pH 9.2) was used in the subsequent experiments.

Binder Example, Entry 20

To water (50.0 g) stirred vigorously at 85° C. was added agar agar (2.63 g) portion-wise over approx. 15 minutes. Stirring was continued for 0.5-1 h further at 85° C. until a clear solution was obtained.

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 10.0 g) in water (56.7 g) was stirred at 50° C. for approx. 15-30 min until a clear solution was obtained (pH 4.6). 1M NaOH (4.00 g) was then added (pH 9.1) followed by a portion of the above chestnut tree tannin solution (4.50 g; thus efficiently 1.00 g chestnut tree tannin) and then a portion of the above agar agar solution (20.0 g; thus efficiently 1.00 g agar agar). After stirring for 1-2 minutes further at 50° C., the resulting brown mixture (pH 8.8) was used in the subsequent experiments.

Binder Example, Entry 21

To water (50.0 g) stirred vigorously at 85° C. was added pectin (2.63 g) portion-wise over approx. 15 minutes. Stirring was continued for 0.5-1 h further at 85° C. until a clear solution was obtained.

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 10.0 g) in water (56.7 g) was stirred at 50° C. for approx. 15-30 min until a clear solution was obtained (pH 4.6). 1M NaOH (4.50 g) was then added (pH 9.6) followed by a portion of the above chestnut tree tannin solution (4.50 g; thus efficiently 1.00 g chestnut tree tannin) and then a portion of the above pectin solution (20.0 g; thus efficiently 1.00 g pectin). After stirring for 1-2 minutes further at 50° C., the resulting brown mixture (pH 8.9) was used in the subsequent experiments.

Binder Example, Entry 22

To water (50.0 g) stirred vigorously at 85° C. was added sodium alginate (2.63 g) portion-wise over approx. 15 minutes. Stirring was continued for 0.5-1 h further at 85° C. until a clear solution was obtained.

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 10.0 g) in water (56.7 g) was stirred at 50° C. for approx. 15-30 min until a clear solution was obtained (pH 4.6). 1M NaOH (4.00 g) was then added (pH 9.2) followed by a portion of the above chestnut tree tannin solution (4.50 g; thus efficiently 1.00 g chestnut tree tannin) and then a portion of the above sodium alginate solution (20.0 g; thus efficiently 1.00 g sodium alginate). After stirring for 1-2 minutes further at 50° C., the resulting brown mixture (pH 9.0) was used in the subsequent experiments.

Binder Example, Entry 23

To water (50.0 g) stirred vigorously at 85° C. was added soluble starch (2.63 g) portion-wise over approx. 15 minutes. Stirring was continued for 0.5-1 h further at 85° C. until a clear solution was obtained.

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 10.0 g) in water (56.7 g) was stirred at 50° C. for approx. 15-30 min until a clear solution was obtained (pH 4.8). 1M NaOH (4.00 g) was then added (pH 9.1) followed by a portion of the above chestnut tree tannin solution (4.50 g; thus efficiently 1.00 g chestnut tree tannin) and then a portion of the above soluble starch solution (20.0 g; thus efficiently 1.00 g soluble starch). After stirring for 1-2 minutes further at 50° C., the resulting brown mixture (pH 8.8) was used in the subsequent experiments.

TABLE 1-1

| | Reference binder |
|---|---|
| Example | A |
| Binder properties | |
| Binder solids (%) | 15.0 |
| Reaction loss (%) | 28.5 |
| pH | 9.6 |
| Bar curing conditions | |
| Temperature (° C./1 h) | 200 |
| Bar properties | |
| Mechanical strength, unaged (kN) | 0.39 |
| Mechanical strength, aged (kN) | 0.28 |
| LOI, unaged (%) | 2.8 |

TABLE 1-2

Polyelectrolytic hydrocolloids, other hydrocolloids

| | Example | | | | | | | | | | |
|---|---|---|---|---|---|---|---|---|---|---|---|
| | 1 | 2 | 3 | 4 | 5 | 6 | 7 | 8 | 9 | 10 | 11 |
| Binder composition Polyelectrolytic hydrocolloid (%-wt.) | | | | | | | | | | | |
| Gelatine, Speisegelatine, 120 bloom | 100 | 100 | — | — | — | — | — | 90 | 90 | 90 | 90 |
| Gelatine, Speisegelatine, 180 bloom | — | — | 100 | 100 | — | — | — | — | — | — | — |
| Gelatine, Imagel LB, 122 bloom | — | — | — | — | 100 | 100 | — | — | — | — | — |
| Pectin | — | — | — | — | — | — | — | — | — | 10 | — |
| Sodium alginate | — | — | — | — | — | — | — | — | — | — | 10 |
| Sodium carboxymethyl cellulose | — | — | — | — | — | — | 100 | — | — | — | — |
| Other hydrocolloid (%-wt.) | | | | | | | | | | | |
| Agar agar | — | — | — | — | — | — | — | 10 | — | — | — |
| Gellan gum | — | — | — | — | — | — | — | — | 10 | — | — |
| Soluble starch | — | — | — | — | — | — | — | — | — | — | — |
| Crosslinker (%-wt.) [a] | | | | | | | | | | | |
| Chestnut tree tannin | — | — | — | — | — | — | — | — | — | — | — |
| Base (%-wt.) [b] | | | | | | | | | | | |
| Sodium hydroxide | — | — | — | — | — | — | — | — | — | — | — |
| Binder mixing and bar manufacture | | | | | | | | | | | |
| Mixing temperature (° C.) | 50 | 50 | 50 | 50 | 50 | 50 | 85 | 50/85 | 50/85 | 50/85 | 50/85 |
| Binder component solids content (%) | 15.0 | 10.0 | 15.0 | 10.0 | 15.0 | 10.0 | 5.0 | 12.5 | 12.5 | 12.5 | 12.5 |
| pH | 5.1 | 4.9 | 5.2 | 4.9 | 5.1 | 5.0 | 8.4 | 5.3 | 5.3 | 4.8 | 5.3 |
| Pre-heated shots (35-40° C.) | — | — | Yes | Yes | — | — | — | — | — | — | — |
| Curing Temperature (° C./15 min to rt) | rt | rt | rt | rt | rt | rt | rt | rt | rt | rt | rt |
| Bar properties | | | | | | | | | | | |
| Mechanical strength, unaged (kN) | 0.31 | 0.24 | 0.28 | 0.13 | 0.20 | 0.13 | 0.13 | 0.11 | 0.09 | 0.13 | 0.13 |
| Mechanical strength, aged (kN) | 0.30 | 0.28 | 0.27 | 0.17 | 0.22 | 0.15 | 0.15 | 0.15 | 0.11 | 0.14 | 0.22 |
| LOI, unaged (%) | 2.9 | 1.9 | 2.9 | 1.9 | 2.8 | 1.9 | 1.9 | 2.4 | 2.5 | 2.4 | 2.3 |

[a] Of hydrocolloid(s).
[b] Of hydrocolloid(s) + crosslinker.

TABLE 1-3

Polyelectrolytic hydrocolloids, other hydrocolloids, crosslinkers

| | Example | | | | | | | | | | | |
|---|---|---|---|---|---|---|---|---|---|---|---|---|
| | 12 | 13 | 14 | 15 | 16 | 17 | 18 | 19 | 20 | 21 | 22 | 23 |
| Binder composition | | | | | | | | | | | | |
| Polyelectrolytic hydrocolloid (%-wt.) | | | | | | | | | | | | |
| Gelatine, Speisegelatine, 120 bloom | 100 | 100 | 100 | 100 | — | — | — | — | 91 | 91 | 91 | 91 |
| Gelatine, Speisegelatine, 180 bloom | — | — | — | — | 100 | 100 | — | — | — | — | — | — |
| Gelatine, Imagel LB, 122 bloom | — | — | — | — | — | — | 100 | 100 | — | — | — | — |
| Pectin | — | — | — | — | — | — | — | — | — | 9 | — | — |
| Sodium alginate | — | — | — | — | — | — | — | — | — | — | 9 | — |
| Sodium carboxymethyl cellulose | — | — | — | — | — | — | — | — | — | — | — | — |
| Other hydrocolloid (%-wt.) | | | | | | | | | | | | |
| Agar agar | — | — | — | — | — | — | — | — | 9 | — | — | — |
| Gellan gum | — | — | — | — | — | — | — | — | — | — | — | — |
| Soluble starch | — | — | — | — | — | — | — | — | — | — | — | 9 |
| Crosslinker (%-wt.) [a] | | | | | | | | | | | | |
| Chestnut tree tannin | 10 | 10 | 10 | 10 | 10 | 10 | 10 | 10 | 9 | 9 | 9 | 9 |
| Base (%-wt.) [b] | | | | | | | | | | | | |
| Sodium hydroxide | 2.7 | 2.6 | 2.6 | 2.6 | 2.4 | 2.4 | 2.4 | 2.4 | 2.4 | 2.5 | 2.4 | 2.4 |
| Binder mixing and bar manufacture | | | | | | | | | | | | |
| Mixing temperature (° C.) | 50 | 50 | 50 | 50 | 50 | 50 | 50 | 50 | 50/85 | 50/85 | 50/85 | 50/85 |
| Binder component solids content (%) | 10.4 | 15.0 | 15.0 | 15.0 | 15.1 | 15.1 | 15.1 | 15.1 | 12.9 | 12.9 | 12.9 | 12.9 |
| pH | 9.2 | 9.1 | 9.1 | 9.1 | 9.2 | 9.2 | 9.2 | 9.2 | 8.8 | 8.9 | 9.0 | 8.8 |
| Pre-heated shots (35-40° C.) | — | — | — | — | Yes | Yes | — | — | — | — | — | — |
| Curing Temperature (° C./15 min to rt) | rt | rt | 35 | 55 | 35 | 55 | 35 | 55 | rt | rt | rt | rt |
| Bar properties | | | | | | | | | | | | |
| Mechanical strength, unaged (kN) | 0.16 | 0.23 | 0.26 | 0.27 | 0.30 | 0.27 | 0.25 | 0.27 | 0.16 | 0.18 | 0.17 | 0.18 |
| Mechanical strength, aged (kN) | 0.15 | 0.21 | 0.25 | 0.25 | 0.25 | 0.31 | 0.27 | 0.26 | 0.15 | 0.13 | 0.15 | 0.18 |
| LOI, unaged (%) | 1.9 | 2.7 | 2.7 | 2.7 | 2.7 | 2.8 | 2.8 | 2.8 | 2.4 | 2.6 | 2.4 | 2.4 |

[a] Of hydrocolloid(s).
[b] Of hydrocolloid(s) + crosslinker

The invention claimed is:

1. A method of bonding together surfaces of two or more elements at least one of which is a mineral wool element bonded by a mineral wool binder, wherein the method comprises providing the two or more elements, applying an adhesive to one or more of the surfaces to be bonded together before, during or after contacting the surfaces to be bonded together with each other and curing the adhesive, the adhesive comprising an aqueous binder composition for mineral fibers, which composition comprises one or more polyelectrolytic hydrocolloids and is capable of being cured at a temperature of not higher than 95° C.

2. The method of claim 1, wherein the one or more polyelectrolytic hydrocolloids comprise one or more hydrocolloids selected from the group consisting of gelatin, pectin, alginate, carrageenan, gum arabic, xanthan gum, and cellulose derivatives.

3. The method of claim 1, wherein one of the one or more polyelectrolytic hydrocolloids is gelatin.

4. The method of claim 1, wherein the composition comprises at least two polyelectrolytic hydrocolloids, one polyelectrolytic hydrocolloid being gelatin and at least one other polyelectrolytic hydrocolloid being selected from the group consisting of pectin, alginate, carrageenan, gum arabic, xanthan gum, and cellulose derivatives.

5. The method of claim 4, wherein gelatin is present in a concentration of from 10 to 95 wt.-%, based on a weight of the at least two polyelectrolytic hydrocolloids.

6. The method of claim 1, wherein the composition comprises at least two polyelectrolytic hydrocolloids which have complementary charges.

7. The method of claim 1, wherein the composition comprises one or more proteins of animal origin and wherein the composition further comprises at least one enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), catechol oxidase, tyrosine oxidase, phenoloxidase, lysyl oxidase (EC 1.4.3.13), and peroxidase (EC 1.11.1.7).

8. The method of claim 1, wherein the composition consists essentially of water, the one or more polyelectrolytic hydrocolloids; optionally at least one oil; optionally at least one pH-adjuster; optionally at least one crosslinker; optionally at least one anti-fouling agent; optionally at least one anti-swelling agent.

9. A method of bonding together surfaces of two or more elements at least one of which is a mineral wool element bonded by a mineral wool binder, wherein the method comprises providing the two or more elements, applying an adhesive to one or more of the surfaces to be bonded together before, during or after contacting the surfaces to be bonded together with each other and curing the adhesive, the adhesive comprising an aqueous binder composition for mineral fibers, which composition comprises at least two polyelectrolytic hydrocolloids, one polyelectrolytic hydrocolloid being gelatin and at least one other polyelectrolytic hydrocolloid being selected from the group consisting of pectin, alginate, carrageenan, gum arabic, xanthan gum, and cellulose derivatives.

10. The method of claim 9, wherein gelatin is present in a concentration of from 10 to 95 wt.-%, based on a weight of the at least two polyelectrolytic hydrocolloids.

11. The method of claim 9, wherein the composition comprises one or more proteins of animal origin and wherein the composition further comprises at least one enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), catechol oxidase, tyrosine oxidase, phenoloxidase, lysyl oxidase (EC 1.4.3.13), and peroxidase (EC 1.11.1.7).

12. A method of bonding together surfaces of two or more elements at least one of which is a mineral wool element bonded by a mineral wool binder, wherein the method comprises providing the two or more elements, applying an adhesive to one or more of the surfaces to be bonded together before, during or after contacting the surfaces to be bonded together with each other and curing the adhesive, the adhesive comprising an aqueous binder composition for mineral fibers, which composition consists essentially of water, one or more polyelectrolytic hydrocolloids; optionally at least one oil; optionally at least one pH-adjuster; optionally at least one crosslinker; optionally at least one anti-fouling agent; optionally at least one anti-swelling agent.

13. The method of claim 12, wherein the one or more polyelectrolytic hydrocolloids comprise one or more hydrocolloids selected from the group consisting of gelatin, pectin, alginate, carrageenan, gum arabic, xanthan gum, and cellulose derivatives.

14. The method of claim 12, wherein one of the one or more polyelectrolytic hydrocolloids is gelatin.

15. The method of claim 12, wherein the composition comprises at least two polyelectrolytic hydrocolloids, one polyelectrolytic hydrocolloid being gelatin and at least one other polyelectrolytic hydrocolloid being selected from the group consisting of pectin, alginate, carrageenan, gum arabic, xanthan gum, and cellulose derivatives.

16. The method of claim 15, wherein gelatin is present in a concentration of from 10 to 95 wt.-%, based on a weight of the at least two polyelectrolytic hydrocolloids.

17. The method of claim 1, wherein the two or more elements comprise at least one element which is not a mineral wool element.

18. The method of claim 9, wherein the two or more elements comprise at least one element which is not a mineral wool element.

19. The method of claim 12, wherein the two or more elements comprise at least one element which is not a mineral wool element.

\* \* \* \* \*